United States Patent
Clough et al.

(10) Patent No.: US 6,268,160 B1
(45) Date of Patent: Jul. 31, 2001

(54) METHOD OF SCREENING FOR ANTI-MALARIAL COMPOUNDS

(75) Inventors: Barbara Clough; Peter Preiser; Robert John Macleod Wilson, all of London (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/140,466

(22) Filed: Aug. 26, 1998

Related U.S. Application Data

(60) Provisional application No. 60/056,246, filed on Aug. 28, 1997.

(51) Int. Cl.⁷ ......................... G01N 33/53; G01N 33/566; G01N 33/569
(52) U.S. Cl. ......................... 435/7.8; 435/7.22; 435/7.93; 435/947; 435/69.1; 435/71.1; 436/501; 436/86; 530/350; 530/822
(58) Field of Search ................. 435/7.22, 6, 7.8, 435/7.93, 69.1, 71.1, 947; 436/501, 86; 530/350, 822

(56) References Cited

U.S. PATENT DOCUMENTS

| | | | |
|---|---|---|---|
| 2,982,689 | * | 5/1961 | Donovick et al. . |
| 3,181,995 | * | 5/1965 | Bodanszky et al. . |
| 4,024,251 | * | 5/1977 | Maiese et al. . |
| 4,062,948 | * | 12/1977 | Vos et al. . |
| 4,218,560 | * | 8/1980 | Maehr . |
| 4,515,783 | * | 5/1985 | Linn et al. . |

FOREIGN PATENT DOCUMENTS

99/02176 * 1/1999 (WO) .

OTHER PUBLICATIONS

McConkey et al., Jan. 24, 1997. Inhibition of *Plasmodium falciparum* protein synthesis. Targeting the plastid–like organelle with thiostrepton. J. Biol. Chem. 272 (4): 2046–2049.*

Kjeldgaard and Nyborg, "Refined Structure of Elongation Factor EF–Tu from *Escherichia coli*", J. Mol. Biol. 223:721–742 (1992).

Garrett, "Antibiotics and active ribosomal RNA sites", TIBS 8(6):189–190 (1983).

Evarsson et al, "Three–dimensional structure of the ribosomal translocase: elongation factor G from *Thermus thermophilus*", The EMBO Journal 13(16):3669–3677 (1994).

Czworkowski et al, "The crystal structure of elongation factor G complexed with GDP, at 2.7 Å resolution", The EMBO Journal 13(16):3661–3668 (1994).

Beckers et al, "Inhibition of Cytoplasmic and Organellar Protein Synthesis in *Toxoplasma gondii*", J. Clin. Invest 95:367–376 (1995).

Black et al, "Activity of Fusidic Acid Against *Plasmodium Falciparum* In Vitro", The Lancet, pp. 578–578 (1985).

Waters, "The Ribosomal RNA Genes of Plasmodium", Adv. Parasitology 39:56–57 (1994).

Coghlan, "Ancient crime may help malaria patients", Science, p. 18, Mar. 15, 1997.

Köhler et al, "A Plastid of Probable Green Algal Origin in Apicomplexan Parasites", Science 275:1485–1489 (1997).

Parmeggiani and Swart, "Mechanism of Action of Kirromycin–Like Antibiotics", Ann. Rev. Microbiol. 39:557–577 (1985).

Feagin et al, "Homologies between the contiguous and fragmented rRNAs of the two *Plasmodium falciparum* extrachromosomal DNAs are limited to core sequences", Nucleic Acids Research 20(4):879–887 (1992).

Gardner et al, Sequence and organization of large subunit rRNA genes from the extrachromosomal 35 kb circular DNA of the malaria parasite *Plasmodium falciparum*, Nucleic Acids Research 21(5):1067–1071 (1993).

Wilson et al, "Complete Gene Map of the Plastid–like DNA of the Malaria Parasite *Plasmodium falciparum*", J. Mol. Biol. 261:155–172 (1996).

Ridley, "Planting the Seeds of New Antimalarial Drugs", Science 285:1502–1503 (1999).

Jomaa et al, "Inhibitors of the Nonmevalonate Pathway of Isoprenoid Biosynthesis as Antimalarial Drugs", Science 285:1573 (1999)—first page only.

Feagin et al, "Indentification of additional rRNA fragments encoded by the *Plasmodium falciparum* 6 kb element", Nucleic Acids Research 25(2):438–446 (1997).

Rogers et al, "Interaction of thiostrepton with an RNA fragment derived from the plastid–encoded ribosomal RNA of the malaria parasite", RNA 3:815–820 (1997).

Clough et al, "Antiobiotic Inhibitors of Organellar Protein Synthesis in *Plasmodium falciparum*", Protist 150:189–195 (1999).

Roy et al, "Protein Synthesis in the Plastid of *Plasmodium falciparum*", Protist 150:183–188 (1999).

Clough et al, "Thiostrepton binds to malarial plastid rRNA", FEBS Letters 406:123–125 (1997).

* cited by examiner

*Primary Examiner*—Christopher L. Chin
*Assistant Examiner*—James L. Grun
(74) *Attorney, Agent, or Firm*—Nixon & Vanderhye P.C.

(57) ABSTRACT

The plastid DNA of the malaria parasite *Plasmodium falciparum* has been sequenced and found to contain a gene encoding an EF-Tu protein. Inhibitors of the protein are effective as anti-malarial compounds and the protein can be used to screen for such inhibitors. Furthermore, the 23S ribosomal RNA encoded on the malaria parasite plastid DNA is a target for anti-malarial compounds and the antibiotic thiostrepton acts as an anti-malarial by binding to the RNA.

2 Claims, 13 Drawing Sheets

Fig.2A.

```
                        10         20         30         40         50
eftu_anani    1  MARAKFERTK PHANIGTIGH VDHGKTTLTA AITTVLAKAG MAKARAY--A   50
eftu_cryph    1  MARDKFERSK PHVNIGTIGH VDHGKTTLTA AISATL-SQY TGKSKKFL--   50
eftu_cyapa    1  MARQKFDGNK PHVNIGTIGH VDHGKTTLTA AITTALASQG KGKARKYD--   50
eftu_pf       1  MNNKLELRNK QHINLGTIGH VDHGKTTLTT AISYLLNLQG LSK--KYNYS   50
eftu_ecoli    1  MSKEKFERTK PHVNVGTIGH VDHGKTTLTA AITTVLAKTY GGAARAFDQ-   50

60         70         80         90        100
eftu_anani   51  DIDAAPEEKA RGITINTAHV EYETCHRHYA HVDCPGHADY VKNMITGAAQ  100
eftu_cryph   51  EIDSAPEEKA RGITINTAHV EYETDKWYYA HVDCPGHADY VKNMITGAAQ  100
eftu_cyapa   51  EIDAAPEEKA RGITINTAHV EYETEKRHYA HVDCPGHADY VKNMITGAAQ  100
eftu_pf      51  DIDSAPEEKI RGITINTTHI EYETLTKHQA HIDCPGHSDY IKNMITGAIQ  100
eftu_ecoli   51  -IDNAPEEKA RGITINTSHV EYDTPTRHYA HVDCPGHADY VKNMITGAAQ  100

110        120        130        140        150
eftu_anani  101  MDGAILVVSA ADGPMPQTRE HILLAKQVGV PNIVVFLNKE DMVDDAELLE  150
eftu_cryph  101  MDGAILVCSA ANGPMPQTRE HILLAKQVGV PYIVVFLNKA DMVDDEELLE  150
eftu_cyapa  101  MDGAILVVSA ADGPMPQTRE HILLAKQVGV PNMVVFLNKE DQIDDADLLE  150
eftu_pf     101  MDIAILVISI IDGIMPQTYE HLLLIKQIGI KNIIIFLNKE DLCDDVELID  150
eftu_ecoli  101  MDGAILVVAA TDGPMPQTRE HILLGRQVGV PYIIVFLNKC DMVDDEELLE  150

160        170        180        190        200
eftu_anani  151  LVELEVRELL SSYDFPGDDI PIVAGSALQA LEAIGGASG  QKS-DNPWVD  200
eftu_cryph  151  LVQLEVQELL EKYDFPGSEI PFVAGSALLA LEAVANNETI KRC-EDKWVD  200
eftu_cyapa  151  LVELEVRELL SKYDFPGDQI PFVSGSALLA LESLSSNPKL MRG-EDKWVD  200
eftu_pf     151  FIKLEVNELL IKYNFDLNYI HLLTGSALNV INILQKNKDY ELIKSNIWTQ  200
eftu_ecoli  151  LVEMEVRELL SQYDFPGDDT PIVRGSALKA LE-------- ---GDAEWEA  200

210        220        230        240        250
eftu_anani  201  KILKLMEEVD AYIPTPEREV DRPFLMAVED VFTITGRGTV ATGRIERGSV  250
eftu_cryph  201  TIYQLMDKVD EYIPTPERET DKAFLMAVED VFSITGRGTV ATGRIERGKV  250
eftu_cyapa  201  KILALMDAVD EYIPTPERPI DKSFLMAIED VFSITGRGTV ATGRIERGAI  250
eftu_pf     201  KLNNLIQIID NII-IFTFKI NDYFLMSIED VFSITGRGTV VTGKIEQSCI  250
eftu_ecoli  201  KILELAGFLD SYIPEPERAI DKPFLLPIED VFSISRGTV  VTGPVERGII  250

260        270        280        290        300
eftu_anani  251  KVGETIEIVG LRI--PRSTI VTGVEMFQKT LDEGLAGDNV GLLLRGIQKT  300
eftu_cryph  251  KVGDTIEIVG LRE--TRNTI ITGLEMFQRS LDEALAGDNV GILVRGIQKT  300
eftu_cyapa  251  KVGETVELVG LKE--FKSTT VTGLEMFQKT LEFGMAGDNI GILLRGVQKT  300
eftu_pf     251  NLNDEIEILK FEKSSPNLTT VIGLEMFKKQ LTQAQSGDNV GILLRNIQKK  300
eftu_ecoli  251  KVGEEVEIVG IKETQ--KST CTGVEMFRKL LDEGRAGENV GVLLRGIKRE  300

310        320        330        340        350
eftu_anani  301  DIERGMVLAK PGSITPHTKF ESEVYVLKKE EGGRHTPFFP GYRPQFYVRT  350
eftu_cryph  301  DIERGMVLAA PGSITPHTKF EGEVYVLTKE EGGRHTPFFS GYRPQFYVRT  350
eftu_cyapa  301  DIERGMVLAK PGSITPHTQF ESEVYVLTKD EGGRHTPFFS GYRPQFYVRT  350
eftu_pf     301  DIKRGMILAT ENKLKVYKST IAETYILTKF EGGRHKPFNI GYKPQFFIRT  350
eftu_ecoli  301  EIERGQVLAK PGTIKPHTKF ESEVYILSKD EGGRHTPFFK GYRPQFYFRT  350

360        370        380        390        400
eftu_anani  351  TDVTGAISDF TADDGSAAEM VIPGDRIKMT VELINPIAIE QGMRFAIREG  400
eftu_cryph  351  TDVTGTIAQF TSDDGSTAEM VMPGDRIKMT AQLIHPIAIE KGMRFAIREG  400
eftu_cyapa  351  TDVTGSIDAF TADDGSNAEM VMPGDRIKMT VSLVHPIAIE QGMRFRIREG  400
eftu_pf     351  VDVTGEIKNI -YLNENVQKV AIPGDKLTLH IELKHYIVLT LNMKFSIREG  400
eftu_ecoli  351  TDVTGTIEL- ----PEGVEM VMPGDNIKMV VTLIHPIAMD DGLRFAIREG  400

410        420        430        440        450
eftu_anani  401  GRTIGAGVVS KIIQ......  ..........  ..........  ..........  450
eftu_cryph  401  GRTVGAGVVS KITE......  ..........  ..........  ..........  450
eftu_cyapa  401  GRTIGAGVVS KIIK......  ..........  ..........  ..........  450
eftu_pf     401  GKTIGAGIIT EIKN......  ..........  ..........  ..........  450
eftu_ecoli  401  GRTVGAGVVA KVLS......  ..........  ..........  ..........  450
```

Fig.2B.

```
ATGAATAATAAATTATTTTTAAGAAATAAACAACATATAAA
TTTAGGTACTATAGGGCATGTAGATCATGGAAAACTACAT
TAACAACAGCTATATCTTATTTATTAAATTTACAAGGATTA
TCAAAAAATATAATTATTCAGATATTGATTCAGCTCCAGA
AGAAAAAATAAGAGGTATTACAATAAATACAACACATATTG
AATATGAAACTTTAACAAACATTGTGCTCATATAGATTGT
CCAGGACATTCCGATTATATTAAAAATATGATTATAGGAGC
CACACAAATGGATATAGCAATTTTAGTAATATCTATAATAG
ATGGTATAATGCCTCAAACTTATGAACATTTATTATTAATA
AAACAAATAGGTATAAAAATATAATTATTTTTTAAATAA
AGAAGATTTATGTGATGATGTTGAATTAATAGATTTTATAA
AATTAGAAGTAAATGAATTATTAATTAAATATAATTTTGAT
TTAAATTATATACATATATTAACTGGTTCAGCATTAAATGT
AATAAATATAATTCAAAAAAATAAGGATTATGAATTAATAA
AATCTAATATTTGGATACAAAAATTAAATAATTTAATTCAA
ATAATTGATAATATTATAATACCTACTAGAAAAATTAATGA
TTACTTTTTAATGTCAATAGAAGATGTATTTTCTATAACAG
GTAGAGGTACAGTAGTAACAGGTAAGATTGAACAAGGATGT
ATAAATTTAAATGATGAAATTGAAATTTTAAAATTTGAAAA
ATCATCTCCTAATTTAACAACAGTTATAGGATTAGAAATGT
TTAAAAAACAATTAACACAAGCACAATCCGGAGATAATGTA
GGTATTTTATTAAGAAATATTCAAAAAAAGATATAAAAAG
AGGTATGATTTTAGCAACACCTAATAAATTAAAAGTATATA
AGTCTTTTATAGCTGAAACATATATTTTAACTAAAGAAGAA
GGTGGTCGTCATAAACCTTTTAATATTGGATATAAACCTCA
ATTTTTTATTCGTACAGTAGATGTTACTGGAGAAATTAAAA
ATATATATTTAAATGAAAATGTACAAAAGTAGCTATACCT
GGAGATAAAATAACATTACATATTGAATTAAAACATTATAT
AGTGTTGACATTAAATATGAAATTTTCTATTAGAGAAGGAG
GAAAAACAATAGGAGCAGGTATTATAACAGAAATAAAAAAT
```

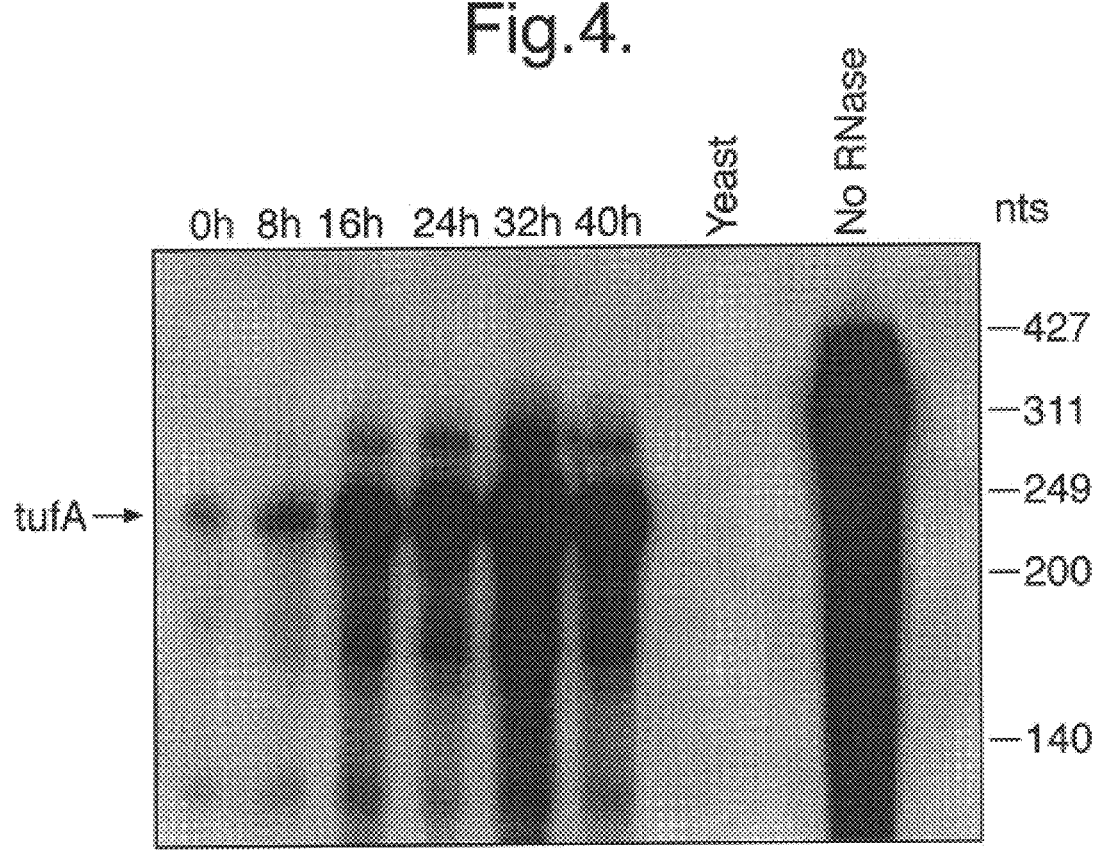

Fig. 5.
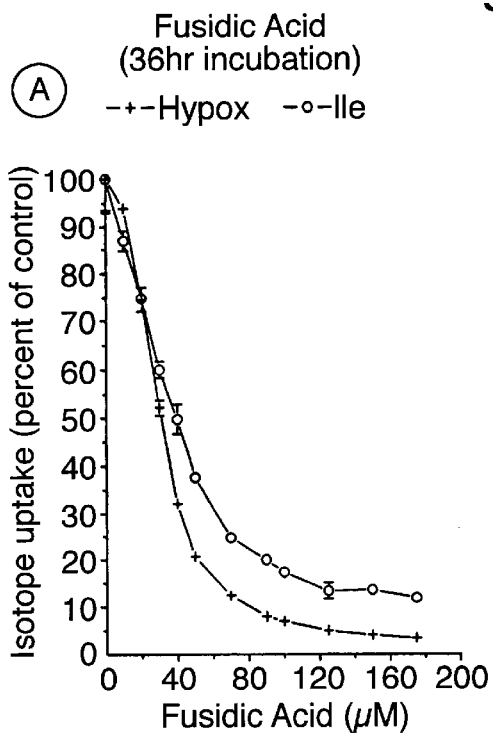
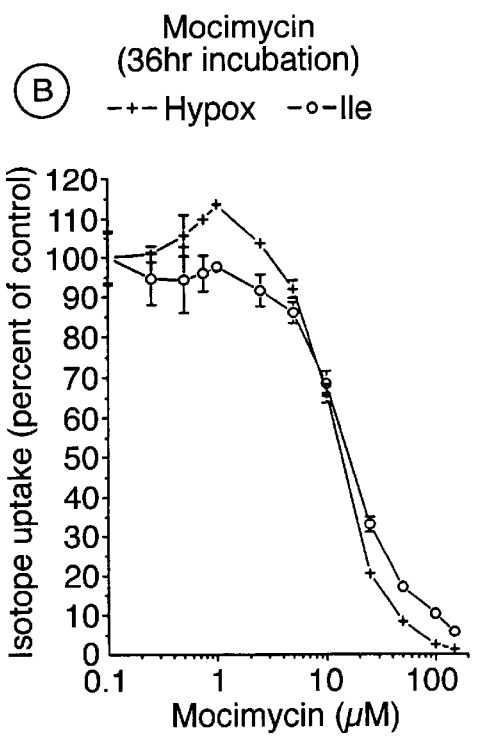
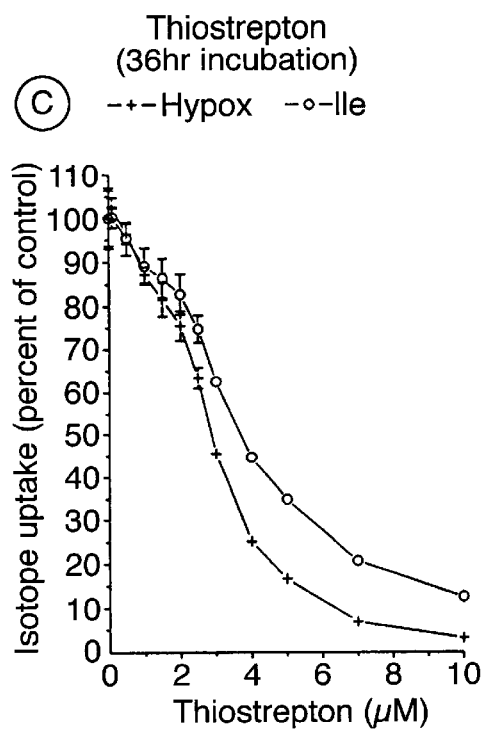
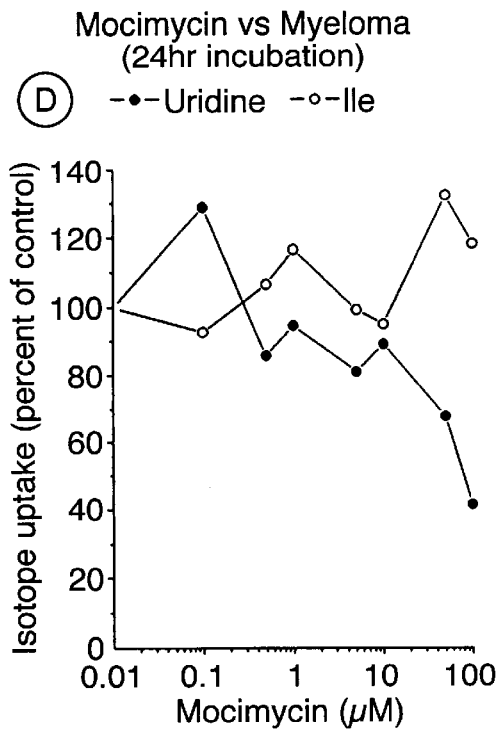

Fig. 5 (Cont). (E)   GE2270
−+− Hypox   −○− Ile
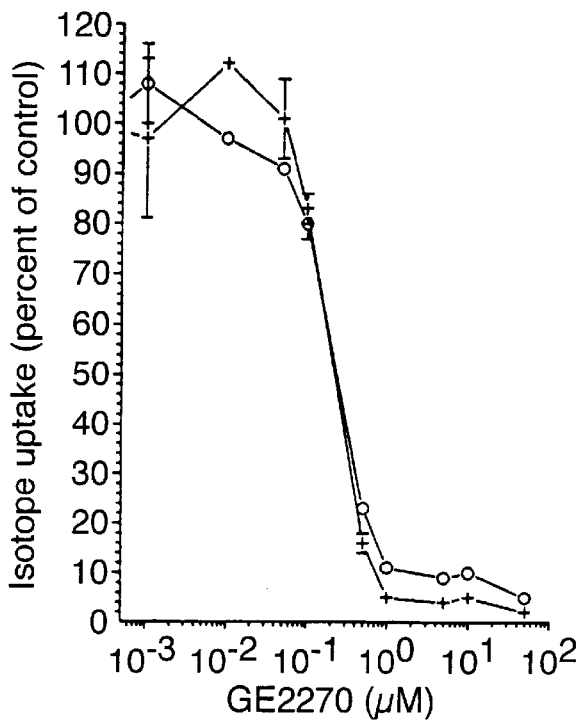
Fig. 6.
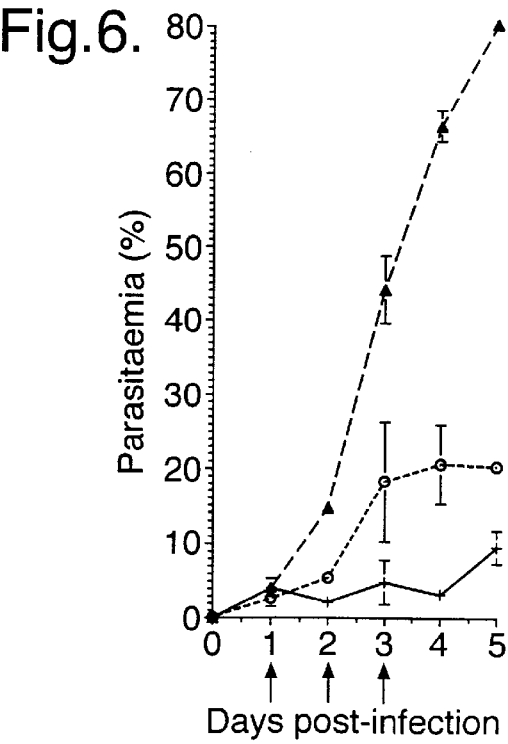

Sequence of the GTPase region of 23Spl rRNAs

Fig. 9.
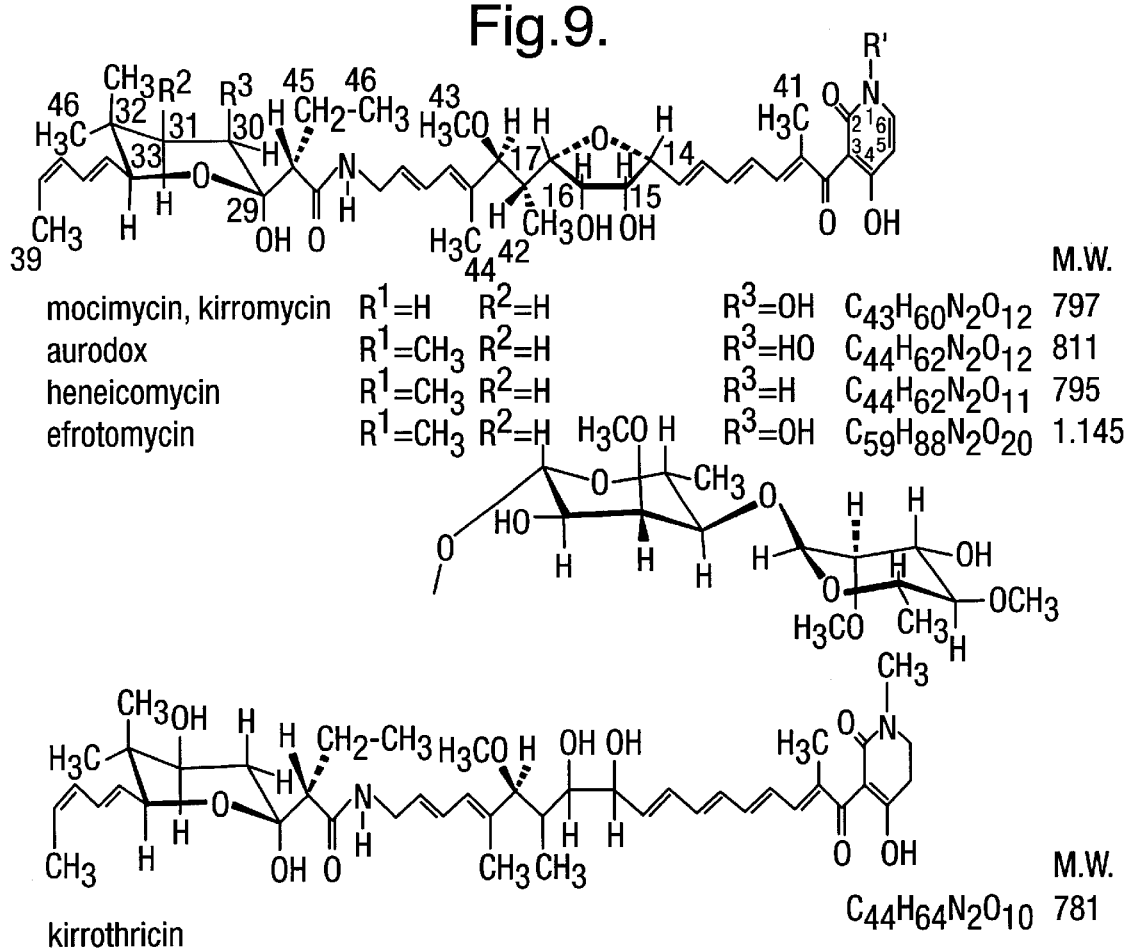
kirrothricin
pulvomycin
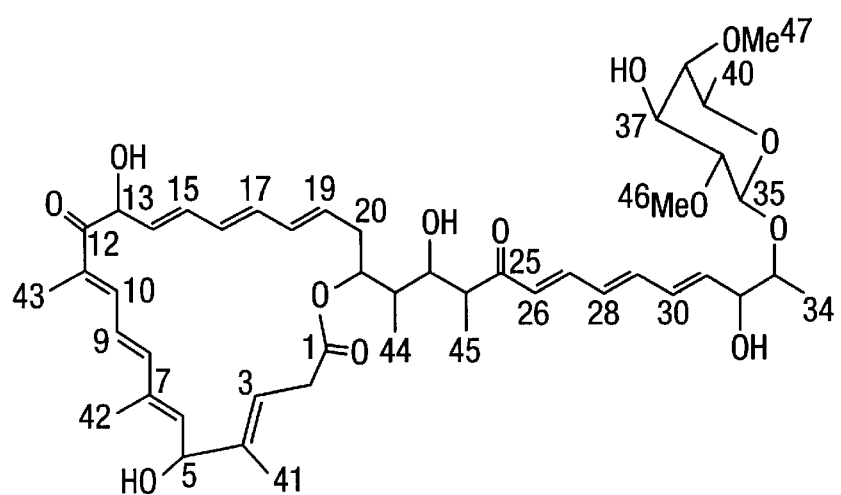

Fig.11.
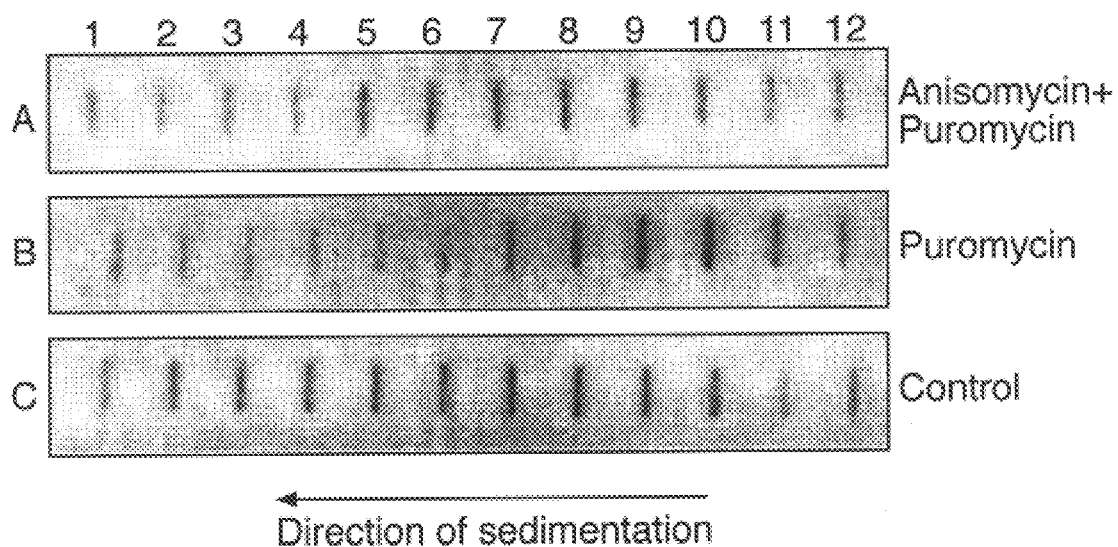
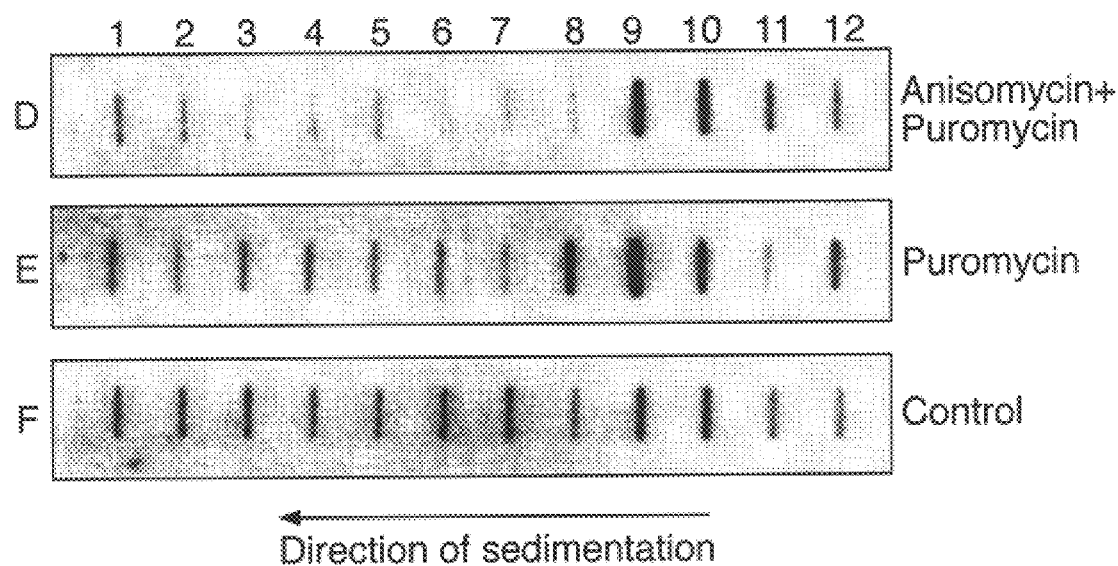

Direction of sedimentation

SEQUENCE LISTING

```
<160> NUMBER OF SEQ ID NOS: 14

<210> SEQ ID NO 1
<211> LENGTH: 1230
<212> TYPE: DNA
<213> ORGANISM: Plasmodium falciparum
<220> FEATURE:
<221> NAME/KEY: CDS
<222> LOCATION: (1)..(1230)

<400> SEQUENCE: 1 atg aat aat aaa tta ttt tta aga aat aaa caa cat ata aat tta ggt        48
Met Asn Asn Lys Leu Phe Leu Arg Asn Lys Gln His Ile Asn Leu Gly
  1               5                  10                  15 act ata ggg cat gta gat cat gga aaa act aca tta aca aca gct ata        96
Thr Ile Gly His Val Asp His Gly Lys Thr Thr Leu Thr Thr Ala Ile
             20                  25                  30 tct tat tta tta aat tta caa gga tta tca aaa aaa tat aat tat tca       144
Ser Tyr Leu Leu Asn Leu Gln Gly Leu Ser Lys Lys Tyr Asn Tyr Ser
         35                  40                  45
```

-continued

```
gat att gat tca gct cca gaa gaa aaa ata aga ggt att aca ata aat    192
Asp Ile Asp Ser Ala Pro Glu Glu Lys Ile Arg Gly Ile Thr Ile Asn
     50              55                  60 aca aca cat att gaa tat gaa act tta aca aaa cat tgt gct cat ata    240
Thr Thr His Ile Glu Tyr Glu Thr Leu Thr Lys His Cys Ala His Ile
 65              70                  75                  80 gat tgt cca gga cat tcc gat tat att aaa aat atg att ata gga gcc    288
Asp Cys Pro Gly His Ser Asp Tyr Ile Lys Asn Met Ile Ile Gly Ala
                 85                  90                  95 aca caa atg gat ata gca att tta gta ata tct ata ata gat ggt ata    336
Thr Gln Met Asp Ile Ala Ile Leu Val Ile Ser Ile Ile Asp Gly Ile
            100                 105                 110 atg cct caa act tat gaa cat tta tta tta ata aaa caa ata ggt ata    384
Met Pro Gln Thr Tyr Glu His Leu Leu Leu Ile Lys Gln Ile Gly Ile
        115                 120                 125 aaa aat ata att att ttt tta aat aaa gaa gat tta tgt gat gat gtt    432
Lys Asn Ile Ile Ile Phe Leu Asn Lys Glu Asp Leu Cys Asp Asp Val
    130                 135                 140 gaa tta ata gat ttt ata aaa tta gaa gta aat gaa tta tta att aaa    480
Glu Leu Ile Asp Phe Ile Lys Leu Glu Val Asn Glu Leu Leu Ile Lys
145                 150                 155                 160 tat aat ttt gat tta aat tat ata cat ata tta act ggt tca gca tta    528
Tyr Asn Phe Asp Leu Asn Tyr Ile His Ile Leu Thr Gly Ser Ala Leu
                165                 170                 175 aat gta ata aat ata att caa aaa aat aag gat tat gaa tta ata aaa    576
Asn Val Ile Asn Ile Ile Gln Lys Asn Lys Asp Tyr Glu Leu Ile Lys
            180                 185                 190 tct aat att tgg ata caa aaa tta aat aat tta att caa ata att gat    624
Ser Asn Ile Trp Ile Gln Lys Leu Asn Asn Leu Ile Gln Ile Ile Asp
        195                 200                 205 aat att ata ata cct act aga aaa att aat gat tac ttt tta atg tca    672
Asn Ile Ile Ile Pro Thr Arg Lys Ile Asn Asp Tyr Phe Leu Met Ser
    210                 215                 220 ata gaa gat gta ttt tct ata aca ggt aga ggt aca gta gta aca ggt    720
Ile Glu Asp Val Phe Ser Ile Thr Gly Arg Gly Thr Val Val Thr Gly
225                 230                 235                 240 aag att gaa caa gga tgt ata aat tta aat gat gaa att gaa att tta    768
Lys Ile Glu Gln Gly Cys Ile Asn Leu Asn Asp Glu Ile Glu Ile Leu
                245                 250                 255 aaa ttt gaa aaa tca tct cct aat tta aca aca gtt ata gga tta gaa    816
Lys Phe Glu Lys Ser Ser Pro Asn Leu Thr Thr Val Ile Gly Leu Glu
            260                 265                 270 atg ttt aaa aaa caa tta aca caa gca caa tcc gga gat aat gta ggt    864
Met Phe Lys Lys Gln Leu Thr Gln Ala Gln Ser Gly Asp Asn Val Gly
        275                 280                 285 att tta tta aga aat att caa aaa aaa gat ata aaa aga ggt atg att    912
Ile Leu Leu Arg Asn Ile Gln Lys Lys Asp Ile Lys Arg Gly Met Ile
    290                 295                 300 tta gca aca cct aat aaa tta aaa gta tat aag tct ttt ata gct gaa    960
Leu Ala Thr Pro Asn Lys Leu Lys Val Tyr Lys Ser Phe Ile Ala Glu
305                 310                 315                 320 aca tat att tta act aaa gaa gaa ggt ggt cgt cat aaa cct ttt aat   1008
Thr Tyr Ile Leu Thr Lys Glu Glu Gly Gly Arg His Lys Pro Phe Asn
                325                 330                 335 att gga tat aaa cct caa ttt ttt att cgt aca gta gat gtt act gga   1056
Ile Gly Tyr Lys Pro Gln Phe Phe Ile Arg Thr Val Asp Val Thr Gly
            340                 345                 350 gaa att aaa aat ata tat tta aat gaa aat gta caa aaa gta gct ata   1104
Glu Ile Lys Asn Ile Tyr Leu Asn Glu Asn Val Gln Lys Val Ala Ile
```

```
                355                 360                 365
cct gga gat aaa ata aca tta cat att gaa tta aaa cat tat ata gtg    1152
Pro Gly Asp Lys Ile Thr Leu His Ile Glu Leu Lys His Tyr Ile Val
    370                 375                 380 ttg aca tta aat atg aaa ttt tct att aga gaa gga gga aaa aca ata    1200
Leu Thr Leu Asn Met Lys Phe Ser Ile Arg Glu Gly Gly Lys Thr Ile
385                 390                 395                 400 gga gca ggt att ata aca gaa ata aaa aat                            1230
Gly Ala Gly Ile Ile Thr Glu Ile Lys Asn
                405                 410

<210> SEQ ID NO 2
<211> LENGTH: 410
<212> TYPE: PRT
<213> ORGANISM: Plasmodium falciparum

<400> SEQUENCE: 2

Met Asn Asn Lys Leu Phe Leu Arg Asn Lys Gln His Ile Asn Leu Gly
  1               5                  10                  15

Thr Ile Gly His Val Asp His Gly Lys Thr Thr Leu Thr Thr Ala Ile
                 20                  25                  30

Ser Tyr Leu Leu Asn Leu Gln Gly Leu Ser Lys Lys Tyr Asn Tyr Ser
             35                  40                  45

Asp Ile Asp Ser Ala Pro Glu Glu Lys Ile Arg Gly Ile Thr Ile Asn
         50                  55                  60

Thr Thr His Ile Glu Tyr Glu Thr Leu Thr Lys His Cys Ala His Ile
 65                  70                  75                  80

Asp Cys Pro Gly His Ser Asp Tyr Ile Lys Asn Met Ile Ile Gly Ala
                 85                  90                  95

Thr Gln Met Asp Ile Ala Ile Leu Val Ile Ser Ile Ile Asp Gly Ile
            100                 105                 110

Met Pro Gln Thr Tyr Glu His Leu Leu Leu Ile Lys Gln Ile Gly Ile
        115                 120                 125

Lys Asn Ile Ile Ile Phe Leu Asn Lys Glu Asp Leu Cys Asp Asp Val
130                 135                 140

Glu Leu Ile Asp Phe Ile Lys Leu Glu Val Asn Glu Leu Leu Ile Lys
145                 150                 155                 160

Tyr Asn Phe Asp Leu Asn Tyr Ile His Ile Leu Thr Gly Ser Ala Leu
                165                 170                 175

Asn Val Ile Asn Ile Ile Gln Lys Asn Lys Asp Tyr Glu Leu Ile Lys
            180                 185                 190

Ser Asn Ile Trp Ile Gln Lys Leu Asn Asn Leu Ile Gln Ile Ile Asp
        195                 200                 205

Asn Ile Ile Ile Pro Thr Arg Lys Ile Asn Asp Tyr Phe Leu Met Ser
    210                 215                 220

Ile Glu Asp Val Phe Ser Ile Thr Gly Arg Gly Thr Val Val Thr Gly
225                 230                 235                 240

Lys Ile Glu Gln Gly Cys Ile Asn Leu Asn Asp Glu Ile Glu Ile Leu
                245                 250                 255

Lys Phe Glu Lys Ser Ser Pro Asn Leu Thr Thr Val Ile Gly Leu Glu
            260                 265                 270

Met Phe Lys Lys Gln Leu Thr Gln Ala Gln Ser Gly Asp Asn Val Gly
        275                 280                 285

Ile Leu Leu Arg Asn Ile Gln Lys Lys Asp Ile Lys Arg Gly Met Ile
    290                 295                 300
```

```
Leu Ala Thr Pro Asn Lys Leu Lys Val Tyr Lys Ser Phe Ile Ala Glu
305                 310                 315                 320

Thr Tyr Ile Leu Thr Lys Glu Glu Gly Gly Arg His Lys Pro Phe Asn
            325                 330                 335

Ile Gly Tyr Lys Pro Gln Phe Phe Ile Arg Thr Val Asp Val Thr Gly
                340                 345                 350

Glu Ile Lys Asn Ile Tyr Leu Asn Glu Asn Val Gln Lys Val Ala Ile
            355                 360                 365

Pro Gly Asp Lys Ile Thr Leu His Ile Glu Leu Lys His Tyr Ile Val
        370                 375                 380

Leu Thr Leu Asn Met Lys Phe Ser Ile Arg Glu Gly Lys Thr Ile
385                 390                 395                 400

Gly Ala Gly Ile Ile Thr Glu Ile Lys Asn
                405                 410

<210> SEQ ID NO 3
<211> LENGTH: 409
<212> TYPE: PRT
<213> ORGANISM: Anacystis nidulans

<400> SEQUENCE: 3

Met Ala Arg Ala Lys Phe Glu Arg Thr Lys Pro His Ala Asn Ile Gly
1               5                   10                  15

Thr Ile Gly His Val Asp His Gly Lys Thr Thr Leu Thr Ala Ala Ile
                20                  25                  30

Thr Thr Val Leu Ala Lys Ala Gly Met Ala Lys Ala Arg Ala Tyr Ala
            35                  40                  45

Asp Ile Asp Ala Ala Pro Glu Glu Lys Ala Arg Gly Ile Thr Ile Asn
        50                  55                  60

Thr Ala His Val Glu Tyr Glu Thr Gly His Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Ala Ile Leu Val Val Ser Ala Ala Asp Gly Pro
                100                 105                 110

Met Pro Gln Thr Arg Glu His Ile Leu Leu Ala Lys Gln Val Gly Val
            115                 120                 125

Pro Asn Ile Val Val Phe Leu Asn Lys Glu Asp Met Val Asp Asp Ala
        130                 135                 140

Glu Leu Leu Glu Leu Val Glu Leu Glu Val Arg Glu Leu Leu Ser Ser
145                 150                 155                 160

Tyr Asp Phe Pro Gly Asp Asp Ile Pro Ile Val Ala Gly Ser Ala Leu
                165                 170                 175

Gln Ala Leu Glu Ala Ile Gln Gly Gly Ala Ser Gly Gln Lys Gly Asp
            180                 185                 190

Asn Pro Trp Val Asp Lys Ile Leu Lys Leu Met Glu Glu Val Asp Ala
        195                 200                 205

Tyr Ile Pro Thr Pro Glu Arg Glu Val Asp Arg Pro Phe Leu Met Ala
210                 215                 220

Val Glu Asp Val Phe Thr Ile Thr Gly Arg Gly Thr Val Ala Thr Gly
225                 230                 235                 240

Arg Ile Glu Arg Gly Ser Val Lys Val Gly Glu Thr Ile Glu Ile Val
                245                 250                 255

Gly Leu Arg Asp Thr Arg Ser Thr Thr Val Thr Gly Val Glu Met Phe
            260                 265                 270
```

```
Gln Lys Thr Leu Asp Glu Gly Leu Ala Gly Asp Asn Val Gly Leu Leu
            275                 280                 285

Leu Arg Gly Ile Gln Lys Thr Asp Ile Glu Arg Gly Met Val Leu Ala
        290                 295                 300

Lys Pro Gly Ser Ile Thr Pro His Thr Lys Phe Glu Ser Glu Val Tyr
305                 310                 315                 320

Val Leu Lys Lys Glu Glu Gly Arg His Thr Pro Phe Phe Pro Gly
                325                 330                 335

Tyr Arg Pro Gln Phe Tyr Val Arg Thr Thr Asp Val Thr Gly Ala Ile
            340                 345                 350

Ser Asp Phe Thr Ala Asp Asp Gly Ser Ala Ala Glu Met Val Ile Pro
        355                 360                 365

Gly Asp Arg Ile Lys Met Thr Val Glu Leu Ile Asn Pro Ile Ala Ile
370                 375                 380

Glu Gln Gly Met Arg Phe Ala Ile Arg Glu Gly Arg Thr Ile Gly
385                 390                 395                 400

Ala Gly Val Val Ser Lys Ile Leu Gln
                405

<210> SEQ ID NO 4
<211> LENGTH: 408
<212> TYPE: PRT
<213> ORGANISM: Cryptomonas phi

<400> SEQUENCE: 4

Met Ala Arg Asp Lys Phe Glu Arg Ser Lys Pro His Val Asn Ile Gly
 1               5                  10                  15

Thr Ile Gly His Val Asp His Gly Lys Thr Thr Leu Thr Ala Ala Ile
                20                  25                  30

Ser Ala Thr Leu Ser Gln Tyr Thr Gly Lys Ser Lys Lys Phe Asp Glu
            35                  40                  45

Ile Asp Ser Ala Pro Glu Glu Lys Ala Arg Gly Ile Thr Ile Asn Thr
        50                  55                  60

Ala His Val Glu Tyr Glu Thr Asp Lys Trp Tyr Tyr Ala His Val Asp
 65                 70                  75                  80

Cys Pro Gly His Ala Asp Tyr Val Lys Asn Met Ile Thr Gly Ala Ala
                85                  90                  95

Gln Met Asp Gly Ala Ile Leu Val Cys Ser Ala Ala Asn Gly Pro Met
            100                 105                 110

Pro Gln Thr Arg Glu His Ile Leu Leu Ala Lys Gln Val Gly Val Pro
        115                 120                 125

Tyr Ile Val Val Phe Leu Asn Lys Ala Asp Met Val Asp Asp Glu Glu
    130                 135                 140

Leu Leu Glu Leu Val Gln Leu Glu Val Gln Glu Leu Leu Glu Lys Tyr
145                 150                 155                 160

Asp Phe Pro Gly Ser Glu Ile Pro Phe Val Ala Gly Ser Ala Leu Leu
                165                 170                 175

Ala Leu Glu Ala Val Ala Asn Asn Pro Thr Ile Lys Arg Gly Glu Asp
            180                 185                 190

Lys Trp Val Asp Thr Ile Tyr Gln Leu Met Asp Lys Val Asp Glu Tyr
        195                 200                 205

Ile Pro Thr Pro Glu Arg Glu Thr Asp Lys Ala Phe Leu Met Ala Val
    210                 215                 220

Glu Asp Val Phe Ser Ile Thr Gly Arg Gly Thr Val Ala Thr Gly Arg
```

```
                    225                 230                 235                 240
Ile Glu Arg Gly Lys Val Lys Val Gly Asp Thr Ile Glu Ile Val Gly
                245                 250                 255

Leu Arg Glu Thr Arg Asn Thr Thr Ile Thr Gly Leu Glu Met Phe Gln
                260                 265                 270

Lys Ser Leu Asp Glu Ala Leu Ala Gly Asp Asn Val Gly Ile Leu Val
            275                 280                 285

Arg Gly Ile Gln Lys Thr Asp Ile Glu Arg Gly Met Val Leu Ala Ala
        290                 295                 300

Pro Gly Ser Ile Thr Pro His Thr Lys Phe Glu Gly Glu Val Tyr Val
305                 310                 315                 320

Leu Thr Lys Glu Glu Gly Gly Arg His Thr Pro Phe Phe Ser Gly Tyr
                325                 330                 335

Arg Pro Gln Phe Tyr Val Arg Thr Thr Asp Val Thr Gly Thr Ile Ala
                340                 345                 350

Gln Phe Thr Ser Asp Asp Gly Ser Thr Ala Glu Met Val Met Pro Gly
            355                 360                 365

Asp Arg Ile Lys Met Thr Ala Gln Leu Ile His Pro Ile Ala Ile Glu
        370                 375                 380

Lys Gly Met Arg Phe Ala Ile Arg Glu Gly Arg Thr Val Gly Ala
385                 390                 395                 400

Gly Val Val Ser Lys Ile Ile Glu
                405

<210> SEQ ID NO 5
<211> LENGTH: 409
<212> TYPE: PRT
<213> ORGANISM: Cyanophora paradoxa

<400> SEQUENCE: 5

Met Ala Arg Gln Lys Phe Asp Gly Asn Lys Pro His Val Asn Ile Gly
  1               5                  10                  15

Thr Ile Gly His Val Asp His Gly Lys Thr Thr Leu Thr Ala Ala Ile
                 20                  25                  30

Thr Thr Ala Leu Ala Ser Gln Gly Lys Gly Lys Ala Arg Lys Tyr Asp
             35                  40                  45

Glu Ile Asp Ala Ala Pro Glu Glu Lys Ala Arg Gly Ile Thr Ile Asn
         50                  55                  60

Thr Ala His Val Glu Tyr Glu Thr Glu Lys Arg His Tyr Ala His Val
 65                  70                  75                  80

Asp Cys Pro Gly His Ala Asp Tyr Val Lys Asn Met Ile Thr Gly Ala
                 85                  90                  95

Ala Gln Met Asp Gly Ala Ile Leu Val Val Ser Ala Ala Asp Gly Pro
            100                 105                 110

Met Pro Gln Thr Arg Glu His Ile Leu Leu Ala Lys Gln Val Gly Val
        115                 120                 125

Pro Asn Met Val Val Phe Leu Asn Lys Glu Asp Gln Ile Asp Asp Ala
    130                 135                 140

Asp Leu Leu Glu Leu Val Glu Leu Glu Val Arg Glu Leu Leu Ser Lys
145                 150                 155                 160

Tyr Asp Phe Pro Gly Asp Gln Ile Pro Phe Val Ser Gly Ser Ala Leu
                165                 170                 175

Leu Ala Leu Glu Ser Leu Ser Ser Asn Pro Lys Leu Met Arg Gly Glu
            180                 185                 190
```

```
Asp Lys Trp Val Asp Lys Ile Leu Ala Leu Met Asp Ala Val Asp Glu
            195                 200                 205

Tyr Ile Pro Thr Pro Glu Arg Pro Ile Asp Lys Ser Phe Leu Met Ala
    210                 215                 220

Ile Glu Asp Val Phe Ser Ile Thr Gly Arg Gly Thr Val Ala Thr Gly
225                 230                 235                 240

Arg Ile Glu Arg Gly Ala Ile Lys Val Gly Thr Val Glu Leu Val
                245                 250                 255

Gly Leu Lys Asp Thr Lys Ser Thr Thr Val Thr Gly Leu Glu Met Phe
            260                 265                 270

Gln Lys Thr Leu Glu Glu Gly Met Ala Gly Asp Asn Ile Gly Ile Leu
        275                 280                 285

Leu Arg Gly Val Gln Lys Thr Asp Ile Glu Arg Gly Met Val Leu Ala
    290                 295                 300

Lys Pro Gly Ser Ile Thr Pro His Thr Gln Phe Glu Ser Glu Val Tyr
305                 310                 315                 320

Val Leu Thr Lys Asp Glu Gly Gly Arg His Thr Pro Phe Phe Ser Gly
                325                 330                 335

Tyr Arg Pro Gln Phe Tyr Val Arg Thr Thr Asp Val Thr Gly Ser Ile
            340                 345                 350

Asp Ala Phe Thr Ala Asp Asp Gly Ser Asn Ala Glu Met Val Met Pro
        355                 360                 365

Gly Asp Arg Ile Lys Met Thr Val Ser Leu Val His Pro Ile Ala Ile
370                 375                 380

Glu Gln Gly Met Arg Phe Arg Ile Arg Glu Gly Gly Arg Thr Ile Gly
385                 390                 395                 400

Ala Gly Val Val Ser Lys Ile Leu Lys
            405

<210> SEQ ID NO 6
<211> LENGTH: 394
<212> TYPE: PRT
<213> ORGANISM: Escherichia coli

<400> SEQUENCE: 6

Met Ser Lys Glu Lys Phe Glu Arg Thr Lys Pro His Val Asn Val Gly
  1               5                  10                  15

Thr Ile Gly His Val Asp His Gly Lys Thr Thr Leu Thr Ala Ala Ile
             20                  25                  30

Thr Thr Val Leu Ala Lys Thr Tyr Gly Gly Ala Ala Arg Ala Phe Asp
         35                  40                  45

Gln Ile Asp Asn Ala Pro Glu Glu Lys Ala Arg Gly Ile Thr Ile Asn
     50                  55                  60

Thr Ser His Val Glu Tyr Asp Thr Pro Thr Arg His Tyr Ala His Val
 65                  70                  75                  80

Asp Cys Pro Gly His Ala Asp Tyr Val Lys Asn Met Ile Thr Gly Ala
             85                  90                  95

Ala Gln Met Asp Gly Ala Ile Leu Val Ala Ala Thr Asp Gly Pro
        100                 105                 110

Met Pro Gln Thr Arg Glu His Ile Leu Leu Gly Arg Gln Val Gly Val
    115                 120                 125

Pro Tyr Ile Ile Val Phe Leu Asn Lys Cys Asp Met Val Asp Asp Glu
130                 135                 140

Glu Leu Leu Glu Leu Val Glu Met Glu Val Arg Glu Leu Leu Ser Gln
145                 150                 155                 160
```

```
Tyr Asp Phe Pro Gly Asp Asp Thr Pro Ile Val Arg Gly Ser Ala Leu
            165                 170                 175
Lys Ala Leu Glu Gly Asp Ala Glu Trp Glu Ala Lys Ile Leu Glu Leu
        180                 185                 190
Ala Gly Phe Leu Asp Ser Tyr Ile Pro Glu Pro Glu Arg Ala Ile Asp
    195                 200                 205
Lys Pro Phe Leu Leu Pro Ile Glu Asp Val Phe Ser Ile Ser Gly Arg
210                 215                 220
Gly Thr Val Val Thr Gly Arg Val Glu Arg Gly Ile Ile Lys Val Gly
225                 230                 235                 240
Glu Glu Val Glu Ile Val Gly Ile Lys Glu Thr Gln Lys Ser Thr Cys
                245                 250                 255
Thr Gly Val Glu Met Phe Arg Lys Leu Leu Asp Glu Gly Arg Ala Gly
            260                 265                 270
Glu Asn Val Gly Val Leu Leu Arg Gly Ile Lys Arg Glu Glu Ile Glu
        275                 280                 285
Arg Gly Gln Val Leu Ala Lys Pro Gly Thr Ile Lys Pro His Thr Lys
    290                 295                 300
Phe Glu Ser Glu Val Tyr Ile Leu Ser Lys Asp Glu Gly Gly Arg His
305                 310                 315                 320
Thr Pro Phe Phe Lys Gly Tyr Arg Pro Gln Phe Tyr Phe Arg Thr Thr
                325                 330                 335
Asp Val Thr Gly Thr Ile Glu Leu Pro Glu Gly Val Glu Met Val Met
            340                 345                 350
Pro Gly Asp Asn Ile Lys Met Val Val Thr Leu Ile His Pro Ile Ala
        355                 360                 365
Met Asp Asp Gly Leu Arg Phe Ala Ile Arg Glu Gly Gly Arg Thr Val
    370                 375                 380
Gly Ala Gly Val Val Ala Lys Val Leu Ser
385                 390

<210> SEQ ID NO 7
<211> LENGTH: 13
<212> TYPE: PRT
<213> ORGANISM: Plasmodium falciparum

<400> SEQUENCE: 7

Ile Gln Lys Asn Lys Asp Tyr Glu Leu Ile Lys Ser Asn
  1               5                   10

<210> SEQ ID NO 8
<211> LENGTH: 58
<212> TYPE: RNA
<213> ORGANISM: Plasmodium falciparum

<400> SEQUENCE: 8
auuaaaaagu aaauuuagaa gcaguuaucu uuuaaagagu gcguaaaagc ucauuaau      58

<210> SEQ ID NO 9
<211> LENGTH: 58
<212> TYPE: RNA
<213> ORGANISM: Plasmodium falciparum

<400> SEQUENCE: 9
auuaaaaagu aaauuuggaa gcaguuaucu uuuaaagagu gcguaaaagc ucauuaau      58

<210> SEQ ID NO 10
```

```
<211> LENGTH: 58
<212> TYPE: RNA
<213> ORGANISM: Plasmodium falciparum

<400> SEQUENCE: 10
auuaaaaagu aaauuuggaa gcaguuaucu uuuaaagagu gcgucaaagc ucauuaau        58

<210> SEQ ID NO 11
<211> LENGTH: 58
<212> TYPE: RNA
<213> ORGANISM: Toxoplasma gondii

<400> SEQUENCE: 11
accagaaggu uagcuuagaa gcaguuuucc uuuaaaaagu gcguaaaagc uuacuggu        58

<210> SEQ ID NO 12
<211> LENGTH: 7
<212> TYPE: PRT
<213> ORGANISM: Escherichia coli

<400> SEQUENCE: 12

Gly His Val Asp His Gly Lys
  1               5

<210> SEQ ID NO 13
<211> LENGTH: 4
<212> TYPE: PRT
<213> ORGANISM: Escherichia coli

<400> SEQUENCE: 13

Asp Cys Pro Gly
  1

<210> SEQ ID NO 14
<211> LENGTH: 4
<212> TYPE: PRT
<213> ORGANISM: Escherichia coli

<400> SEQUENCE: 14

Asn Lys Cys Asp
```

METHOD OF SCREENING FOR ANTI-MALARIAL COMPOUNDS

This application claims the benefit of U.S. Provisional Application No. 60/056,246, filed Aug. 28, 1997, the contents being incorporated by reference.

FIELD OF THE INVENTION

This invention relates to a new protein encoded in the plastid DNA of the malaria parasite *Plasmodium falciparum*, to DNA encoding the protein, to methods of producing the protein, to methods of screening for anti-malarial compounds, to compounds identified by such screening methods and to methods of preventing or treating growth of the malaria parasite.

BACKGROUND TO THE INVENTION

The malarial 35 kb circular DNA molecule central to this invention corresponds to a minor species of DNA distinct from nuclear DNA discovered in the 1960s (Gutteridge et al. 1971). In the mid-80s the first study on its purification and molecular analysis was published (Williamson et al. 1985). Its similarity was noted to a circular DNA in the related organism *Toxoplasma gondii*—a well known opportunistic pathogen in AIDS cases.

It is important to stress that the malaria parasite and related apicomplexans are unusual amongst non-photosynthetic organisms in that they possess two forms of organellar DNA, typically a property of plants. One form of organellar DNA has been identified as mitochondrial DNA (mtDNA), whereas the other, the 35 kb circle, we have proposed is the remnant of a plastid DNA (plDNA), a provenance hitherto unsuspected for these organisms (Wilson et al. 1991, 94). This plDNA was probably acquired by an ancient progenitor of the phylum and may be of algal origin (Williamson et al. 1994). The precise location of these organellar DNAs in the cell shows they are in separate compartments (Kohler et al 1997).

Thus, there are potentially two organellar protein synthesising systems of independent prokaryotic origin within the malaria organism that could be susceptible to inhibition with antibiotics. Although the malarial mitochondrion is the best characterised of the organelles, its genetic content is highly idiosyncratic, contributing only incomplete fragments of two rRNA genes to the machinery required for protein synthesis. The circular DNA from the putative plastid, on the other hand, is much more conventional, producing transcripts of four complete rRNA genes, some twenty tRNA genes, subunits of a typical plastid RNA polymerase, and a number of ribosomal protein genes organised in modified bacterial operons.

SUMMARY OF THE INVENTION

In sequencing the malarial plastid DNA, we found that it contains a gene encoding a new EF-Tu protein homologous to the EF-Tu proteins known in prokaryotes. Thus, the invention provides an EF-Tu protein encoded on the plastid DNA of the malaria parasite *Plasmodium falciparum*. The invention also provides DNA encoding the protein.

The prokaryotic EF-Tu proteins are known to be important in controlling the elongation cycle in protein synthesis, and it is known that inhibition of the proteins by various compounds has an antibiotic effect. In view of the sequence similarity between the prokaryotic EF-Tu proteins and our newly-identified malarial plastid EF-Tu protein, we proposed the theory that the antibiotic compounds which inhibit the prokaryotic proteins may also inhibit the malarial protein and therefore be useful as anti-malarials. We tested such antibiotics (e.g. kirromycin and aurodox) for their anti-malarial effect and found our theory was correct; the antibiotics were found to be effective anti-malarials both in vitro and in vivo. Thus, the invention provides a method of preventing or treating infection of a patient with the malaria parasite *Plasmodium falciparum*, which method comprises administering to the patient a compound which inhibits the EF-Tu protein encoded on the plastid DNA of said malaria parasite.

The knowledge provided by the invention of the EF-Tu protein in the malaria plastid and the fact that its inhibitors are effective anti-malarials allows the protein to be used in screening for new anti-malarial compounds. Accordingly, the invention includes a method of identifying an anti-malarial compound, which method comprises (i) contacting a test compound with the EF-Tu protein encoded on the plastid DNA of the malaria parasite *Plasmodium falciparum*; and (ii) determining whether the compound binds to or inhibits the protein, any such binding or inhibition being indicative that the compound is an anti-malarial.

We also investigated the ability of antibiotics which bind to other components of the prokaryotic protein synthesis machinery to act as anti-malarial compounds. As a result of these investigations, it was found that thiostrepton, which is known to bind to the GTPase domain of the 23S ribosomal RNA of *E. coli*, is also able to bind to GTPase domain of the 23S rRNA encoded on the plastid of the malaria parasite *Plasmodium falciparum* (Pf 23S rRNA$_{pl}$). Accordingly, the invention provides a method of identifying an anti-malarial compound, which method comprises (i) contacting the compound with the 23S ribosomal RNA encoded on the plastid DNA of the malaria parasite *Plasmodium falciparum* (Pf 23S rRNA$_{pl}$) or with a fragment of said RNA containing the GTPase domain; and (ii) determining whether the compound binds to said RNA or said fragment, any such binding being indicative that the compound is an anti-malarial.

BRIEF DESCRIPTION OF THE DRAWINGS

FIG. 2A shows the amino acid sequence (SEQ ID NO:2) of the EF-Tu protein according to the invention from the plastid of the malaria parasite *Plasmodium falciparum* (pf). The sequence is aligned with sequences of EF-Tu proteins from other organisms, namely *E. coli* ("ecoli", SEQ ID NO:6), *Anacystis nidulans* ("anani", SEQ ID NO:3), *Cyanophora paradoxa* ("cypha", SEQ ID NO:5) and *Cryptomonas phi* ("cryph", SEQ ID NO:4).

FIG. 2B shows the nucleotide sequence of the tufA gene (SEQ ID NO:1) that encodes the EF-Tu protein according to the invention.

FIG. 4 shows the results of an experiment in which an antisense RNA probe (about 230 nts) made by in vitro transcription, corresponding to a portion of the tufA gene encoding domains I and II of the predicted EF-Tu$_{pl}$ protein, was used in an RNase protection assay to demonstrate the presence of tufA transcripts in total RNA extracted from erythrocytic parasites during the course of a single growth cycle (0–40 hrs).

FIG. 5 shows dose-response curves for the effects of fusidic acid, (FIG. 5A), mocimycin (FIG. 5B) (kirromycin), thiostrepton (FIG. 5C) and GE 2270 (FIG. 5E) on incorporation of $^3$H-hypoxanthine and $^{14}$C-isoleucine into erythrocytic stages of P. falciparum grown in cultures over a 36 hour period. The FIGURE also shows a dose-response curve for the effect of mocimycin on myeloma cells (a control) (FIG. 5D).

FIG. 6 shows the effects of aurodox and mocimycin on the growth of P. chabaudi in mice. The solid line is for aurodox, the dotted line is for mocimycin and the dashed line is for no drug controls. The arrows on the x-axis indicate days on which three 0.1 ml 100 mM ip injections were given.

FIGS. 9 and 10 show the structures of various antibiotics usable in the invention.

FIG. 11 shows slot blots of RNA fractioned on sucrose gradients. Pretreatment with anisomycin blocked the puromycin-induced shift of the hybridization signal for P.falciparum cytosolic 23S ribosomes but not the plastid 16S ribosomes. A–C. Blots hybridized with a probe for the cytosolic large subunit (23S) rRNA. Anisomycin blocked the puromycin-induced shift. D–F. The same blots hybridized with a probe for the plastid-encoded small subunit (16S) rRNA. Anisomycin did not block the puromycin-induced shift.

DETAILED DESCRIPTION OF THE INVENTION

The EF-Tu Protein

Figure 1:
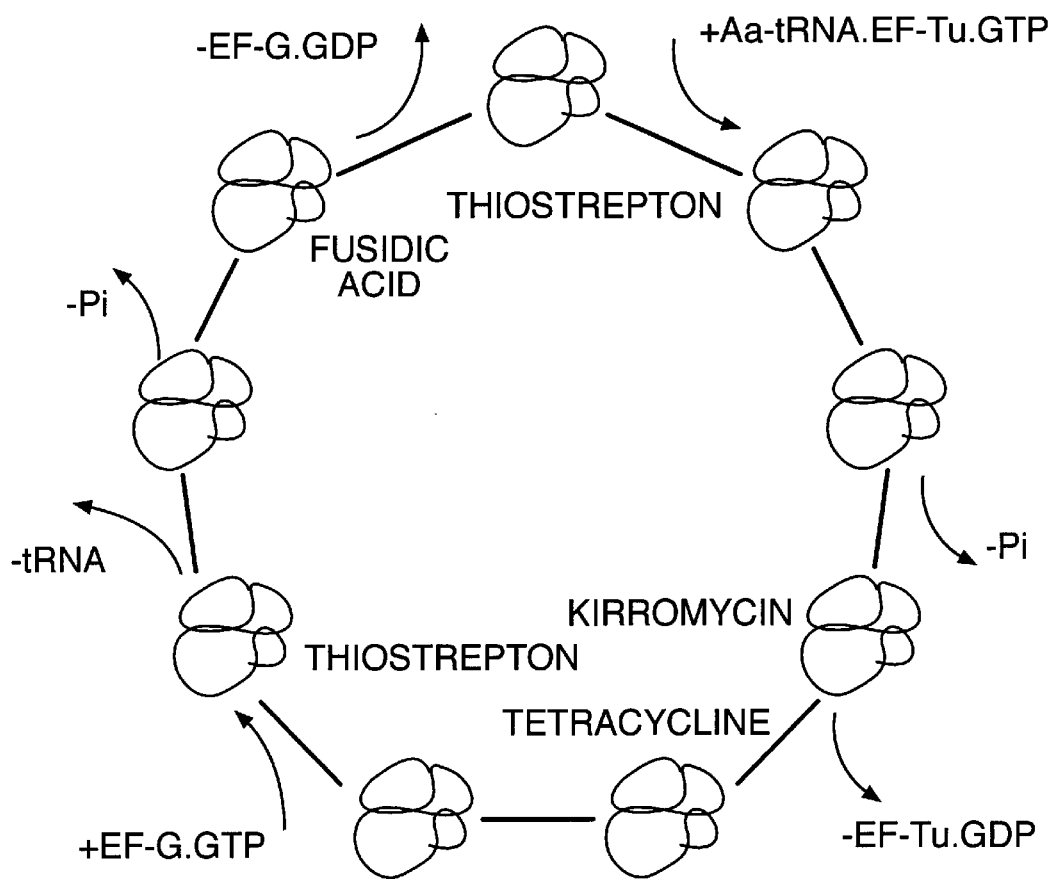
FIG. 1 is a schematic illustration of the elongation cycle that occurs during protein synthesis and shows the points in the cycle at which various inhibitors operate.

The function of the EF-Tu protein is in the elongation cycle of protein synthesis. The cycle is illustrated in FIG. 1.

EF-Tu reacts with GTP and AA-tRNA to form an EF-Tu/AA-tRNA/GTP complex. After binding to EF-Tu, the AA-tRNA component is transferred to the ribosomal A site with the release of free EF-Tu-GDP complex and phosphate. The GDP is released from EF-Tu and the EF-Tu is then ready for another cycle.

EF-Tu is an exceedingly abundant protein in E. coli, present in approximately as many copies as there are tRNA molecules. It can bind every tRNA except for fMet-tRNA.

The malarial plastid EF-Tu has much sequence identify with known EF-Tu proteins from other organisms (see FIG. 2A). We have made a 3D-model structure for the malarial plastid EF-Tu protein based on the crystal structures available for bacterial equivalents (E. coli and T. thermophilus). This model showed that the bacterial and malarial proteins are very similar indeed, strongly implying that the malarial plastid EF-Tu is functional.

The sequence of the malarial plastid EF-Tu protein of the invention may be that labelled "eftu_pf" in FIG. 2A, but variations in this sequence are possible. The protein may, for example, have a sequence identity with the sequence in FIG. 2A of 80% or more, 90% or more, 95% or more or 99% or more.

The sequence of FIG. 2A may be modified by substitution, deletion, extension or insertion. A substitution, deletion or insertion may involve one or more amino acids, typically from 1 to 5, from 1 to 10 or from 1 to 20 amino acids.

Such modified sequences must retain the functions of the EF-Tu protein necessary for participation in the elongation cycle of protein synthesis. In general, the physicochemical nature of the sequence of FIG. 2A should be preserved; the amino acids of a modified sequence should generally be of a similar charge, size and hydrophobicity/hydrophilicity as those in the sequence of FIG. 2A. Candidate substitutions are those in which an amino acid from one of the following groups is replaced by a different amino acid from the same group:

H, R and K

I, L, V and M

A, G, S and T

D and E.

The EF-Tu protein of the invention may be provided in purified form. The protein may also be provided in pure form and in isolated form. The protein may, for example, be provided in a preparation in which it constitutes 10% or more, 40% or more, 80% or more, 90% or more, 95% or more or 99% or more of the total protein in the preparation by weight.

The protein will usually be obtained by expression of recombinant DNA containing the protein, but may also be obtained by biochemical purification of the protein from the malaria parasite.

DNA Encoding the Malarial Plastid EF-Tu Protein

The DNA encoding the EF-Tu protein may have the sequence shown in FIG. 2B, but variations in this sequence are possible. The DNA molecule may, for example, have a sequence identity with the sequence shown in FIG. 2B of 70% or more, 80% or more, 90% or more, 95% or more or 99% or more.

A recombinant DNA molecule encoding the EF-Tu protein of the invention may be obtained using well-known and conventional recombinant DNA techniques, such as those described in Sambrook et al (1989) Molecular Cloning: A Laboratory Manual, 2nd Ed., Cold Spring Harbor Laboratory, Cold Spring Harbor, N.Y.

Such DNA molecules may be obtained by making a library of replicable expression vectors. The library may be created by cloning all the DNA or, more preferably, the plastid DNA of the malaria parasite into a parent vector. The library may be screened for members containing the desired nucleic acid sequence, e.g. by means of a DNA probe or antibody.

The term "replicable expression vector" is used herein to mean a vector which contains the appropriate origin of replication sequence for directing replication of the vector. The vector may also contain the appropriate sequences for expression of the EF-Tu protein. The sequences for expression of the protein will generally include a transcription promotor and a translation initiator operably linked to the coding sequence. The term "operably linked" refers to a linkage in which the promotor and initiator are connected in such a way to the coding sequence as to permit expression of the protein. A vector may, for example, be a plasmid, virus or phage vector. A vector may contain one or more selectable markers, for example an ampicillin resistance gene in the case of a bacterial vector or a neomycin resistance gene in the case of a mammalian vector. A foreign gene sequence encoding the EF-Tu protein inserted into a vector may be transcribed in vitro or the vector may be used to transform a host cell.

According to one embodiment of the invention, there is provided a host cell transformed with a vector encoding the EF-Tu protein. A vector and host cell will be chosen so as to be compatible with each other, and may be prokaryotic or eukaryotic. A prokaryotic host may, for example, be *E.coli* in which case the vector may, for example, be a bacterial plasmid or a phage vector. A eukaryotic host may, for example, be a yeast (e.g. *S.cerevisiae*), a chinese hamster ovary (CHO) cell or an insect cell (e.g. *Spodoptera frugiperda*).

The invention includes a method of producing the EF-Tu protein encoded on the plastid DNA of the malaria parasite *Plasmodium falciparum*, which method comprises
 (i) culturing a host cell containing a DNA molecule encoding the protein under conditions such that the protein is expressed; and
 (ii) recovering the protein from the culture.

Antibodies to the Malarial Plastid EF-Tu Protein

The invention includes an antibody specific for the EF-Tu protein of the invention. The antibody is preferably monoclonal, but may also be polyclonal. The antibody may be labelled. Examples of suitable antibody labels include radiolabels, biotin (which may be detected by avidin or streptavidin conjugated to peroxidase), alkaline phosphatase and fluorescent labels (e.g. fluorescein and rhodamine). The term "antibody" is used herein to include both complete antibody molecules and fragments thereof. Preferred fragments contain at least one antigen binding site, such as Fab and F(ab')$_2$ fragments. Humanised antibodies and fragments thereof are also included within the term "antibody".

The antibody may be produced by raising antibody in a host animal against an EF-Tu protein according to the invention or an antigenic epitope thereof (hereinafter "the immunogen"). Methods of producing monoclonal and polyclonal antibodies are well-known. A method for producing a polyclonal antibody comprises immunising a suitable host animal, for example an experimental animal, with the immunogen and isolating immunoglobulins from the serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein, Nature 256, 495–497, 1975).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Assays for Identifying Anti-malarial Compounds that Inhibit the Malarial Plastid EF-Tu Protein As mentioned above, the knowledge provided by the invention of the EF-Tu protein in the malaria plastid and the fact that its inhibitors are effective anti-malarials allows the protein to be used in screening for new anti-malarial compounds.

Various different assay systems may be used to carry out the screening, but all the assays have in common that the EF-Tu protein of the invention is contacted with test compounds and the ability of each test compound to bind to or inhibit the protein is determined. Any such binding or inhibition is indicative that the compound could be useful as an anti-malarial drug.

The screening assays will generally require one or more controls. It will generally be desirable to include a positive control in the form of a compound known to bind to or inhibit the EF-Tu protein, so as to ensure that the assay system is responding properly. Examples of suitable positive controls include kirromycin (mocimycin) and aurodox (1-methylmocimycin), which we have shown through our experiments to be effective anti-malarials and which are known to inhibit prokaryotic EF-Tu. It will also generally be desirable to include a negative control in the form of a sample containing no test compound, so as to obtain a measurement of the background signal in the assay. If a test compound gives a signal in the assay above that of the background, this is indicative that the compound has given a positive result and could be an anti-malarial.

One convenient type of assay system is a "band shift" system. This involves determining whether a test comopund advances or retards the EF-Tu protein of the invention on gel electrophoresis relative to the EF-Tu protein in the absence of test compound. The mobility of GDP complexed EF-Tu is decreased with GE2270A but increased with enacyloxin IIa or kirromycin.

Another convenient type of assay system is a competitive binding system. Such a system may comprise
 (i) incubating the EF-Tu protein of the invention with a test compound and a labelled reference compound that is known to bind the protein (e.g. kirromycin or aurodox);

(ii) determining the amount of the labelled reference compound that is bound to the protein; and
(iii) comparing the amount of bound labelled reference compound determined in step (ii) with the amount of said compound that binds to the protein in the absence of the test compound;

wherein any reduction in the binding of the labelled reference compound in the presence of the test compound compared to the binding in the absence of the test compound shows that the test compound is competing with the reference compound for binding to the protein and indicates that the test compound could be an anti-malarial.

The amount of the labelled reference compound bound to the protein may be measured directly or indirectly. A direct measurement may be carried out by removing assay mixture containing the unbound labelled reference compound and measuring the amount of label that is in the protein fraction. Alternatively, the amount of labelled reference compound bound to the protein could be determined indirectly by measuring the amount of label remaining in the assay solution after removal of the protein fraction, which will be inversely related to the amount that has bound to the protein.

In a competitive binding assay system, the EF-Tu protein may be immobilised on a solid support or may be in solution.

Suitable labels for use in the assay systems according the invention are well-known in the art and include the labels set out above that may be attached the antibodies of the invention.

Use of Compounds that Inhibit the Malarial Plastid EF-Tu Protein as Anti-malarials Compounds that inhibit the malarial plastid EF-Tu protein may be used as anti-malarial compounds. Such compounds may be identified using the screening assays described above.

We have already identified some such compounds, e.g. the antibiotics kirromycin (mocimycin), aurodox (1-methylmocimcyin), Efrotomycin (a glycoside of kirromycin), Enacyloxin IIa and GE2270. Efrotomycin has previously been shown to have the desirable properties of rapid oral absorption and prolonged plasma half-life.

The antibiotics in the kirromycin series may be represented by the general formula:

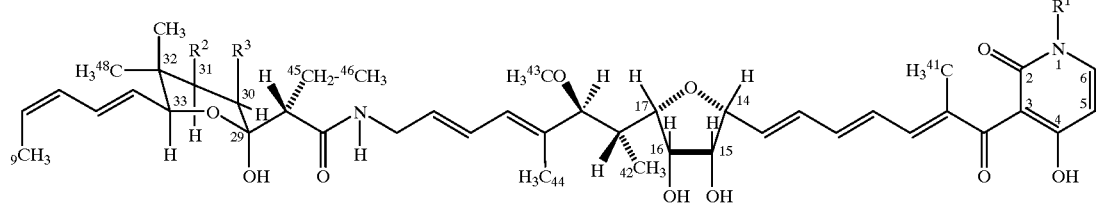

The use of immobilised protein has the advantage that, after the binding reaction is complete, the protein/labelled reference compound complex may be separated from the labelled reference compound that remains in solution by simply removing the solution away from the solid support. If, on the other hand, the protein is not immobilised during the assay but rather is in solution, then it will generally be necessary to devise a means for separating the protein/labelled reference compound complex from the uncomplexed reference compound before measuring the amount of label. Such separation could be achieved, for example, by precipitating the protein using an antibody to the protein or by using a non-specific protein precipitation technique.

wherein $R^1$ is hydrogen or a $C_1$–$C_4$ alkyl group (e.g. methyl); $R^2$ is hydrogen, $C_1$–$C_4$ alkyl or a sugar group (e.g. a disaccharide); and $R^3$ is hydrogen, OH or $C_1$–$C_4$ alkyl.

Preferred antibiotics for use in the invention are as follows:

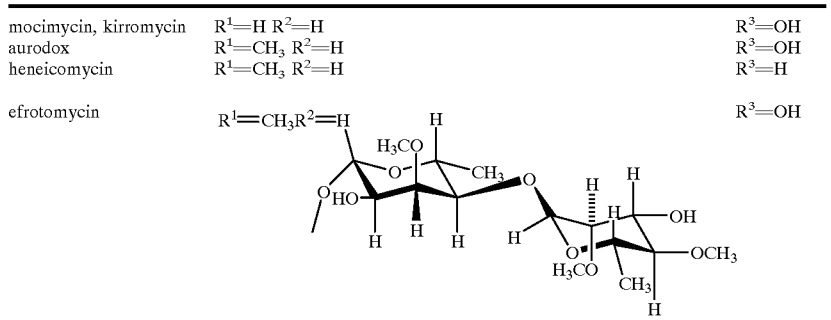

| | | |
|---|---|---|
| mocimycin, kirromycin | $R^1$=H $R^2$=H | $R^3$=OH |
| aurodox | $R^1$=$CH_3$ $R^2$=H | $R^3$=OH |
| heneicomycin | $R^1$=$CH_3$ $R^2$=H | $R^3$=H |
| efrotomycin | $R^1$=$CH_3$ $R^2$=H | $R^3$=OH |

The compounds may be used in either the treatment of an existing infection by the malaria parasite or in the prevention of such an infection from occurring in the first place. The dosage regimen will ultimately be at the discretion of the physician, who will take into account factors such as the nature of the compound, the severity of any disease and the weight and age of the patient. However, suitable routes of administration may include the oral route, the rectal route, the intramuscular route and the intravenous route. The oral route is preferred because this is generally the most convenient route for a patient to take regular doses of the compound without the assistance of a physician. A typical dose would be from 1 to 1000 mg and such a dose may, for example, be taken from 1 to 3 times daily.

In order to be administered to a patient, the compound will be provided in the form of a pharmaceutical composition containing the active compound and a pharmaceutically acceptable carrier or diluent. Typical oral dosage compositions include tablets, capsules, liquid solutions and liquid suspensions.

Compounds that Bind to the 23S rRNA Encoded on the Malaria Parasite

We have found that the 23S rRNA encoded on the plastid of the malaria parasite *Plasmodium falciparum* (Pf 23S rRNA$_{pl}$) is a target for compounds with anti-malarial activity. More specifically, we have found that the mechanism of action of the antibiotic thiostrepton, which was known to have anti-malarial activity, is through binding to the GTPase domain of the 23S rRNA of the malaria plastid.

This information allows the design of assays for screening for further anti-malarial compounds whose mechanism of action operates through the 23S rRNA. These assays involve contacting each of the test compounds with the 23S rRNA or a fragment thereof containing the GTPase binding domain, and measuring any binding of the test compounds to the rRNA or fragment. Any such binding is of course indicative that the compound could be an anti-malarial.

We have already developed one assay for detecting binding to the 23S rRNA. We made a short transcript from DNA encoding the 23S rRNA of the malaria plastid corresponding to the GTPase domain (about nucleotide 1051 to about nucleotide 1108) and found that the transcript bound thiostrepton strongly.

The binding was specific. It depended to a large extent on the presence of an A residue at the position corresponding to *E. coli* position 1067. A transcript corresponding to the GTPase domain of the *E. coli* 23S rRNA (which contained the A at position 1067) was also shown to bind thiostrepton strongly. Mutation of A1067 to either U or G in the malaria plastid transcript dramatically reduced binding. A transcript corresponding to the GTPase domain of the cytosolic malaria 28S rRNA also bound thiostrepton poorly.

A screening assay for further anti-malarial compounds can be based on a competitive binding assay in which the ability of each test compound to compete with thiostrepton for binding to the Pf 23S rRNA$_{pl}$ is measured. Such an assay comprises (i) incubating the Pf 23S rRNA$_{pl}$ or a fragment thereof containing the GTPase domain with the test compound and thiostrepton as a reference compound (or another reference compound known to bind to the rRNA or the fragment);

(ii) determining the amount of thiostrepton (or other reference compound) that is bound to the rRNA or the fragment; and (iii) comparing the amount of thiostrepton (or other reference compound) bound to the rRNA or the fragment with the amount that is bound in the absence of the test compound;

wherein any reduction in the binding of the thiostrepton (or other reference compound) in the presence of the test compound compared to the binding in the absence of the test compound is indicative that the test compound is competing for binding to the rRNA and that the test compound could be an anti-malarial.

In a screening assay based on the invention for further anti-malaria compounds, it would be necessary to use appropriate controls. A good positive control would be to use a compound known to compete with thiostrepton (or with the other reference compound) to ensure that the assay is working properly; a positive result for the known competitor in the assay would indicate that the assay had worked correctly. It would also generally be desirable to use a negative control comprising, for example, a sample in which no thiostrepton or test compound is present; this would enable the background signal in the assay to be determined and any signal above the background would indicate binding to the 23S rRNA.

The following experiments serve to illustrate the invention.

EXPERIMENTAL SECTION

Materials and Methods

Polysome preparation and puromycin shift—*P. falciparum* was grown in blood cultures (Trager et al 1976) and ribosomes prepared as described (Sherman et al 1975). Parasitized erythrocytes were lysed for 1 hr on ice in a buffer containing 0.14% Nonidet P-40 (Trade Name), 25 mM KCl, 10 mM MgCl$_2$, 380 mM sucrose, 6.5 mM β-mercaptoethanol and 50 mM Tris HCl, pH 7.6. The lysate was centrifuged ×3 at 10,000 g for 10 min at 4° C. to remove genomic DNA and other cell debris before further centrifugation at 105,000 g for 1 hr in an SW40 rotor (Trade Name, Beckman) at 4° C. The resulting pellet was resuspended in 25 mM KCl, 5 mM MgCl$_2$ and 50 mM Tris HCl (pH 7.6) and homogenized by hand (×50 strokes) with a glass ounce homogenizer (Wheatstone, USA). The suspension was centrifuged at 10,000 g for 10 min at 4° C. and the crude pellet discarded before further centrifugation for 2 hr at 105,000 g in an SW55 rotor (Beckman) at 4° C. The pellet was resuspended in 10 mM Tris HCl, 10 mM MgCl$_2$, 100 mM KCl and homogenized again to give a suspension of ribosomes.

Polysomes were fractioned on sucrose gradients (20–50% w/v) prepared in 0.3M KCl, 3 mM MgCl$_2$ and 1 mM dithiothreitol (DDT) with 0.02M Tris HCl (pH 7.6)-referred to as "high salt" buffer; centrifugation was at 30,000 g (Beckman Sw40 rotor) for 21 hr at 4° C.

In an experiment with RNase (Cox 1969), total polysomes were incubated with a range of concentrations of RNase (1–13 ng ml$^{-1}$ ribosomes, Boehringer) prior to centrifugation for 30 min at 26° C. In other experiments, polysomes were dissociated to monosomes and subunits by the incorporation of puromycin; here the total ribosome preparation was incubated for 20 min at 37° C. with 2 mM puromycin in the "high salt" buffer to which was added 2 mM GTP, 10 μlml$^{-1}$ RNAsin (39 Uμl$^{-1}$, Promega) and 1 mM DTT. In some experiments, ribosomes were incubated with both anisomycin (Sigma) and puromycin. Anisomycin was added at 3 mM for 10 min at 37° C. followed by incubation with puromycin as above (Cundliffe et al 1974). After ribosome fractionation on the sucrose gradients, RNA was extracted with phenol/chloroform/isoamyl alcohol (Chomczynski it al 1987), precipitated in ethanol and blotted on to nylon membranes (Gene Screen, Trade Name) using a slot-blot apparatus (Scot-Labs). Hybridization was carried out with $^{32}$P-labelled DNA prepared from either cloned fragments of the 35 kb plDNA of *P. falciparum*, PCR products amplified from it, oligonucleotides based on its sequence (Wilson et al 1996), or with PCR products based on the sequence of Pf 28S cytosolic rRNA (McCutchen et al 1988). Hybridization signals were quantitated using a Molecular Dynamics phosphor imager.

Antibiotics—Samples of Mocimycin (kirromycin), Aurodox (N-methylated kirromycin), and Efrotomycin (a glycoside of kirromycin) were used. Aurodox was dissolved in RPMI-Albumax medium (Grande et al 1977), kirromycin was dissolved in RPMI made alkaline by addition of 1M NaOH, and efrotomycin was dissolved in ethanol before dilution in culture medium. Enacyloxin IIA was dissolved in 1% $NaHCO_3$ prior to dilution in RPMI-Albumax medium. The antibiotic GE2270A was dissolved in 100% DMSO before dilution in culture medium. Fusidic acid (Sigma) was dissolved directly in culture medium, and thiostrepton (Sigma) in 100% DMSO before dilution in culture medium. A hemisuccinate form of thiostrepton was prepared as a potassium salt, according to Bodanszky et al 1965. Incorporation of radiotracers by *P.falciparum* growing in blood cultures in the presence and absence of drugs was carried out as described (Strath et al 1993).

EF-Tu model—Pf EF $Tu_{pl}$ was modelled by homology with the known 3D structures determined by X-ray crystallography of EF-Tu.GTP (Berchtold et al 1993) and EF-Tu.GDP (Polekhina et al 1996) both from *Thermus aquaticus*. Modelling was carried out with the WHAT-IF program package (Trade Name, Vriend 1990), as described in Tews et al 1996. Alignments had to be adjusted manually because of small gaps and insertions. An iterative procedure of the automated model-building algorithm checked and corrected the alignments until no errors were detectable. Three insertions in the Pf $EF-Tu_{pl}$ sequence had to be deleted: Leu 190, Pro263 and Leu359-Val363. The final alignment with the *T. aquaticus* structure had single residue gaps in the Pf sequence between Leu41 and Ser42 as well as residues Asn209 and Ile2 10. Co-ordinates for the C (alpha) backbone were copied from the known structure for overlapping segments and the atoms for the amino acids Gly, Ala and Pro were placed directly in their calculated positions. All remaining residues were assigned to Ala before the order in which side changes had to be placed was calculated by the algorithm implemented by the program. Atoms were subsequently placed using a position-dependent amino acid rotamer library. The model was refined geometrically and re-numbered according to the *P.falciparum* sequence.

Heterologous expression—The malarial plastid tufA gene was amplified by PCR, cloned into the TA vector (Trade Name, Invitrogen) and its sequence determined (Wilson et al 1996). Re-cloning into the expression vector pGEX (Trade Name, Pharmacia) was carried out with a PCR product generated using 5' and 3' primers providing custom-made restriction sites. Transfectants in *E.coli* (strains DH5 alpha, Sure, JM109) were found mostly to carry deletions within the tufA sequence, but one clone in JM109 contained the complete insert (sequenced on a single strand). This was expressed as a fusion protein of the expected size by induction of mid-log phase cultures with 50 $\mu$M isopropyl-β-D-thiogalactoside (IPTG) at 37° C. or 27° C. The insoluble fusion protein was solubilized in 5M guanidinium HCl and refolded by dilution (Lin et al 1991).

Antibody to an epitope of Pf EF-Tu—A rabbit polyclonal antibody was prepared against a 13-mer synthetic peptide IQKNKDYELIKSN (SEQ ID NO:7) from domain I of Pf EF-Tu coupled to polylysine beads (Severn Biotech. Ltd). In Western blots (ECL protocol, Amersham), this antibody did not cross-react with EF-Tu from *E.coli*, nor did an antibody to *E.coli* EF-Tu react with the expressed malarial protein.

Drug binding—Thiostrepton binding to short rRNA transcripts generated in vitro was assayed according to Ryan et al 1991, as modified by Clough et al 1997. A band shift method in native 12% polyacrylamide gel (Cetin et al 1996) was used to demonstrate complex formation between a resolubilized fraction of the expressed Pf $EF-Tu_{pl}$ and various antibiotics. Before electrophoresis and immunoblotting, samples were incubated on ice for 15 mins in 50 mM imidazole acetate (pH 7.6), 10 mM $NH_4Cl$, 10 mM $MgCl_2$, 1 mM DDT and 100 $\mu$M GDP, in a final volume of 20 $\mu$l.

Results
Evidence for Plastid Protein Synthesis

Ribosomes from erythrocytic parasites were fractionated by centrifugation on linear gradients (20–50% sucrose) and RNA was extracted from fractions collected over the length of the gradients. Slot blots of the RNA were hybridized with $^{32}$P-labelled DNA probes prepared from either cloned fragments of Pf plDNA, PCR products based on its sequence, or kinased oligonuceotides. As shown in FIG. 11 C&F, hybridization with probes for the large$_{(cytosolic)}$ or small$_{(plastid)}$ subunit rRNAs gave signals extending to the bottom of the gradient, indicative of rRNA incorporated in polysomes. Supportive evidence was obtained by limited digestion of the total ribosome preparation with RNase (13 ng RNase/mg ribosomes for 30 min at 26° C.) before fractionation—this causes dissociation of the polysomes (Cox 1969) and shifted the hybridization signal up the gradient (data not shown). More specific evidence for a subset of polysomes belonging to the plastid compartment was obtained by incubating total ribosomes with 2 mM puromycin in the presence of GTP, 0.3M KCl and 1 mM DDT prior to density gradient fractionation: puromycin acts as an analogue of the 3' terminal adenosine of aminoacylated tRNAs and is incorporated into nascent peptide chains, terminating translation and dissociating polysomes (Gale et al 1981). Incubation with puromycin caused a shift of both the cytosolic and plastid rRNA hybridization signals up the gradient (FIG. 11, B&E). The specificity of the puromycin-shift was confirmed by pretreating Pf ribosomes with the antibiotic anisomycin which binds only to eukaryotic ribosomes and prevents puromycin incorporation (Gale et al 1981). As shown in FIG. 11A, anisomycin blocked the puromycin-induced shift of the hybridization signal for Pf 28S cytosolic rRNA, whereas hybridization of the same blot with a probe for Pf 16S $rRNA_{pl}$ showed the puromycin-shift of the plastid subset of polysomes was not blocked (FIG. 11D).

Figure 12:
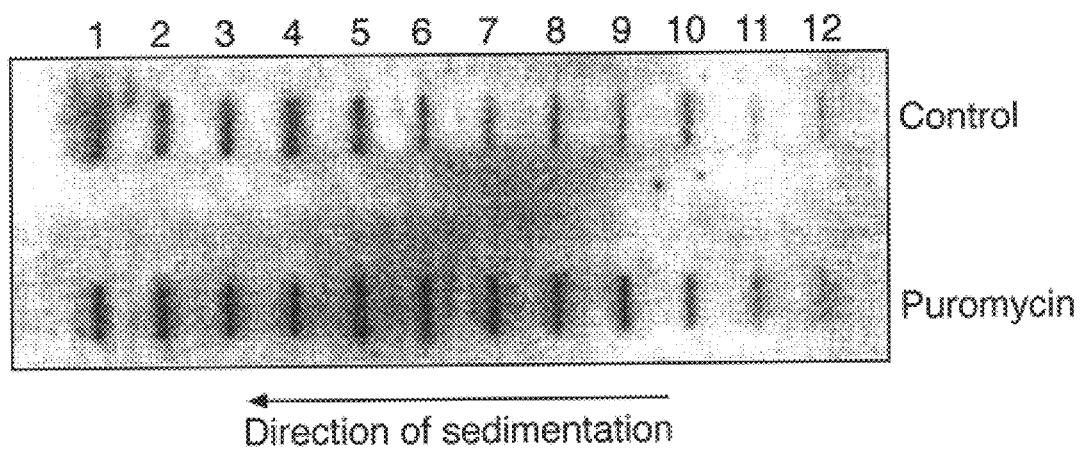
FIG. 12 is a slot blot showing the puromycin-induced shift of the hybridization signal for plastid mRNA specifying EF-Tu.

Similar results were obtained with a probe for an mRNA specified by the plDNA. FIG. 12 shows the puromycin-induced shift of the hybridization signal for mRNA specifying $EF-Tu_{pl}$.

To quantitate the relative proportions of the hybridization signals generated by different species of RNA, slot blots were hybridized with $^{32}$P-labelled oligonucleotides, known amounts of DNA being used as appropriate standards. The 28S cytosolic rRNA was estimated to be 80-fold more plentiful than 16S rRNApl and 2000-fold more plentiful than the mRNA specifying $EF-Tu_{pl}$ (data not shown). These results and the puromycin-shifts are consistent with the presence of actively translating plastid ribosomes in blood cultures of malaria parasites.

tufA Sequence

From a combination of cloned DNA fragments and PCR products amplified from the 35 kb circular DNA of *P.falciparum*, we derived a 1.23 kb nt sequence whose predicted peptide (calculated M.Wt. 46,633) is homologous to the elongation factor EF-Tu (FIG. 2A). The malarial gene lies 45 nts downstream from two ribosomal protein-encoding genes, rps12 and rps7. In this respect, the organization resembles the str operon on the plDNAs of the flagellate protists *Euglena gracilis* (Montadon & Stutz, 1984; Hallick et al. 1993) and *Astasia longa* (Seimelster et al. 1990), as well as the non-chlorophyte alga Cryptomonas (Douglas, 1991), and the cyanelle of *Cryptomonas paradoxa* (Kraus et al. 1990), the intervening fus gene encoding EF-G in the str operon of bacteria such as *E.coli* (Zengal and Lindahl BBA 1050, 317 (1990)) presumably having been transferred to the nucleus. The short intergenic region upstream of the PfpltufA gene does not contain an open reading frame or putative leader sequence. At the nt level, the malarial pltufA gene is extremely rich in adenine and thymine (A+T) residues (79%) compared to related sequences in the database, a feature with important consequences for computations intended to establish the gene's phylogenetic relationships.

At the predicted peptide level, the malarial sequence is very divergent from other recorded EF-Tu's (only 45% amino acid identity with *E.coli* and 51% identity with *Anacystis nidulans*). Nonetheless, several highly conserved regions are evident, including the four segments of domain I involved in GTP binding. In *E.coli*, the first three of these segments carry the consensus elements G18HVDHGK24 (SEQ ID NO:12); D80CPG83(SEQ ID NO:13); and N135KCD138(SEQ ID NO:14). In the malarial sequence there is only one substitution C136E. Most of the residues defining the GDP binding pocket also are conserved (in *E.coli* G23, N135, K136, D138, S173, L175), the only substitution in the malarial sequence being M139L. In a less well conserved region (amino acids 180–190, topologically close to the GTP binding domain), the malarial sequence has an insertion typical of plastid versions of EF-Tu that is not found in the *E.coil* gene, and is only partially present in the mitochondrial equivalent (tufM) of *Saccharomyces cerevisiae* (Nagata et al. 1983). Despite the gene's high A+T content, the predicted malarial EF-Tu peptide is one of the most highly conserved proteins encoded by the 35 kb circle; however, it is potentially more basic (calculated pI=8.43) than the versions present in bacteria or the yeast mitochondrion (Piechulla & Kuntzel, 1983).

In view of the unknown functional status of the 35 kb circular DNA, it was of interest to compare the predicted malarial EF-Tu$_{pl}$ peptide with the unusual chloroplast form in the Charophycean alga *Colochaete orbicularis*, as it has been suggested that the latter may no longer be functional, there being multiple tufA-like sequences in the nucleus (Baldauf et al. 1990). Baldauf and colleagues pointed out that the *C.orbicularis* EF-Tu$_{pl}$ amino acid sequence differs in twenty two sites that otherwise are conserved in all but four of 27 other EF-Tu sequences. Despite the malarial gene's extreme A+T content, the predicted EF-Tu peptide has only 6 conservative amino acid substitutions in the same 22 residues (Table 1). This suggests that the functional domains encoded by the tufA gene on the 35 kb circle have been m aintained under selective pressure.

TABLE 1

AMINO ACID SEQUENCE COMPARISON OF CONSENSUS SITES (MODIFIED FROM BALDAUF ET AL. 1990)

| Site* | C | cp | eub | all | Pf |
|---|---|---|---|---|---|
| 21–22 | FS | VD | VD | VD | VD |
| 60–62 | NMS | GIT | GIT | GIT | GIT |
| 87 | N | D | D | D | D |
| 90 | N | K | K | K | K |
| 128 | I | V | V | V | V |
| 153 | N | E | E | E | E |
| 210 | L | I | I | I | I |
| 227 | R | D | D | D | D |
| 233 | S | G | G | G | G |

TABLE 1-continued

AMINO ACID SEQUENCE COMPARISON OF CONSENSUS SITES (MODIFIED FROM BALDAUF ET AL. 1990)

| Site* | C | cp | eub | all | Pf |
|---|---|---|---|---|---|
| 236 | L | T | T | T | T |
| 241 | T | R | R | R | K |
| 248 | N | K | K | K | N |
| 272 | K | E | E | E | E |
| 286 | D | N | N | N | N |
| 301 | K | R | R | R | R |
| 372 | E | D | D | D | D |
| 393 | V | A | A | A | S |
| 401 | I | V | V | V | I |
| 405 | I | V | V | V | I |

Figure 3A:
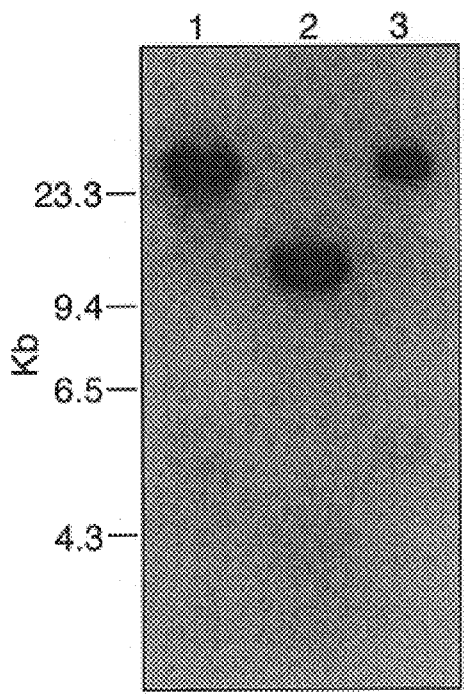
FIG. 3A shows a Southern blot of endonuclease-restricted malarial genomic DNA hybridised with a PftufA-specific PCR product as probe. A single band for the 35 kb plastid was obtained for each restriction digest.
Figure 3B:
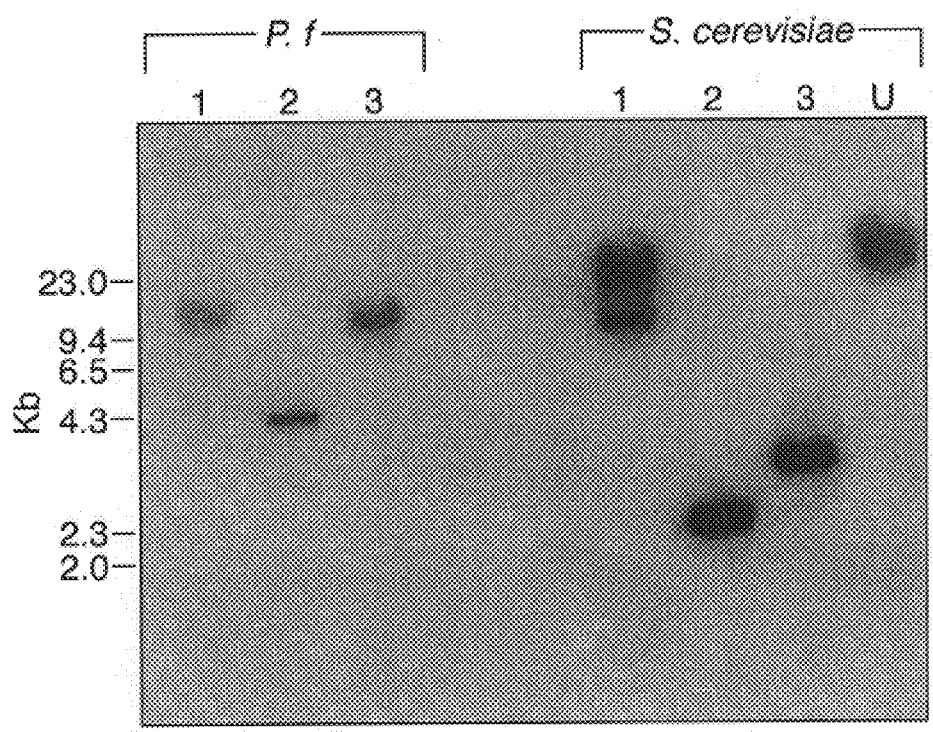
FIG. 3B shows cross-hybridisation between endonuclease-restricted malarial genomic DNA and the yeast tufM gene, indicating the possible presence of a malarial version of tufM.

* = Amino acids numbered as in FIG. 2A.
C = *Coleochaete orbicularis* chloroplast tuf A (Baldauf et al. 1990)
cp = cyanobacteria and chloroplast consensus
eub = eubacteria, cyanobacteria and chloroplast consensus
all = eubacteria, eukaryotes and archaebacteria consensus
Pf = *Plasmodium falciparum* 35 kb circule tufA When hybridized with a PftufA-specific PCR product under stringent conditions, Southern blots of endonuclease-restricted malarial genomic DNA gave a single band of the size predicted (FIG. 3A). At low stringency no other bands were revealed that might have corresponded to the nucleus-encoded mitochondrial gene tufM (Nagata et al, 1983; Wells et al. 1994). The likely presence of a malarial equivalent was indicated, however, by cross-hydridization at low stringency with a PCR product based on the yeast tufM gene (FIG. 3B).

An antisense RNA probe (~230 nts) made by in vitro transcription, corresponding to a portion of the malarial tufA gene encoding domains I and II of the predicted EF-Tu$_{pl}$ protein, was used in an RNase protection assay to demonstrate the presence of tufA transcripts in total RNA extracted from erythrocytic parasites (FIG. 4).

Modelling of the Three-dimensional Structure of *P.falciparum* EF-Tu$_{pl}$.

Despite the highly divergent amino acid composition of Pf EF-Tu$_{pl}$, a computer model showed conservation of secondary structure motifs in all three domains of the hypothetical protein. The model is reliable, with good confidence in the overall folding and also in the detail of the secondary structure compared with *T.aquaticus*. Only minor differences were found in the length of some structural motifs: in domain I there are small length differences in 5 of the nine alpha helices and in 3 out of six β strands. The changes are more pronounced in domain II where the first two β-strands seem to be continuous in Pf, and an extra β-strand is formed by residues Gly245-Leu249. In domain III, differences from *T. aquaticus* are again minor with a slightly different positioning of two β-strands.

The model for Pf EF-Tu$_{pl}$.GTP showed that the GTP-binding site is conserved as well as the whole lining towards the GTP-binding pocket. There is also conservation on the interface between the domains. These interfaces are exposed when EF-Tu. GTP converts to the effective EF-Tu.GDP form. In this form of the protein, conserved residues in the cleft between domains I and III correspond to the site which other studies have shown kirromycin binds.

Antibiotics

The effects of three classes of compounds on intraerythrocytic parasites of *P.falciparum* in vitro, as well as on *P.chabaudi* in vivo, are considered below. In assessing the significance of these results it should be noted that in prokaryotes, kirromycin, whose binding site is at the interface of domains I and III of-EF-Tu.GTP (Mesters et al.

1994), binds to the ternary complex of tRNA and EF-Tu.GTP preventing the conformational change required for release from the ribosome upon GTP hydrolysis, whereas the drug has a different effect on eukaryotic cells. In the latter, at 100µM, it blocks RNA synthesis without affecting DNA or protein synthesis (Schmid et al. 1978).

Kirromycin: Kirromycin-resistant forms of bacterial EF-Tu are modified at one of seven amino acids along the opposing interfaces of domains I and III (Mesters et al 1994 and Abdulkarim et al 1994) and Pf EF-Tu$_{pl}$ has a substitution at one of these sites (A375S-$E.coli$ numbers) that could potentially confer resistance to kirromycin. To test this possibility, kirromycin (Mocimycin), its methylated derivative Aurodox or its disaccharide derivative Efrotomycin were incubated with erythrocytic stages of $P.falciparum$ grown in cultures over a 36 hr period. The incorporation of both $^3$H-hypoxanthine and $^{14}$C-isoleucine was inhibited in a dose-dependent fashion, maximum inhibition being achieved at 100µM kirromycin (FIG. 5). Similar levels of inhibition were obtained for all three compounds. In synchronized cultures, inhibitory effects on ring stage parasites were observed as early as five hours after exposure to Aurodox and were maximal after 10 hrs exposure. Once maximal depression of incorporation had been reached at any particular dose of drug, residual incorporation continued at a uniform rate thereafter. Vital staining with rhodamine 123, a fluorescent dye that concentrates within the mitochondrion (Divo et al. 1985) confirmed the parasiticidal effect, loss of specific mt staining being evident within 2–3 hours (data not shown). Treatment of parasites with 1 mM Aurodox for 1.5 cell cycles, followed by removal of the antibiotic by washing and follow-up for 2 weeks in vitro, indicated the effect was parasite death rather than stasis. Blood cultures of $P.falciparum$ were about 10 times more sensitive to the antibiotic than a gram-positive bacterium (Corynebacterium spp) used in parallel bioassays.

On the basis of these findings, preliminary studies were carried out on mice infected with $P.chabaudi$. In the first experiment, mice were infected and inoculated on the same day intraperitoneally with 0.1 ml of 100 mM Aurodox, a dose calculated to mimic the maximal inhibitory effect observed in vitro. The Aurodox-treated animals showed a lag in development of the infection compared with untreated controls indicating partial inactivation of the infectious inoculum (FIG. 6). In a single experiment, Mocimycin was found to be less effective in vivo than Aurodox.

Enacyloxin IIa: Enacyloxin IIa (ExIIa) is a linear antibiotic representing a new family of polyenic antibiotics (Watanabe 1992) that bind to EF-Tu and block transfer to the nascent peptide chain of aminoacylated-tRNA bound at the A site (Cetin 1996). The profiles for inhibition of radiotracer incorporation in blood cultures of $P.falciparum$ incubated with Ex IIa were similar to those with Mocimycin.

GE2270: This is a thiopeptide antibiotic in the same family as thiostrepton. It binds to a different site on Ef-Tu than kirromycin and locks the protein into a different conformation (Landini 1996). This antibiotic was more inhibitory in blood cultures than either kirromycin or thiostrepton (FIG. 5).

Fusidic acid: Fusidic acid, presently in clinical use as a narrow spectrum antibiotic, was assessed as a potential antimalarial by titration with $P.falciparum$ in vitro, as described above. Maximum inhibition of radiotracer incorporation was achieved at a concentration of 200 µM (FIG. 5). Preliminary experiments with fusidic acid in mice infected with $P. chabaudi$ found little effect on parasitaemias, even at toxic dose levels of the drug.

Figure 7:
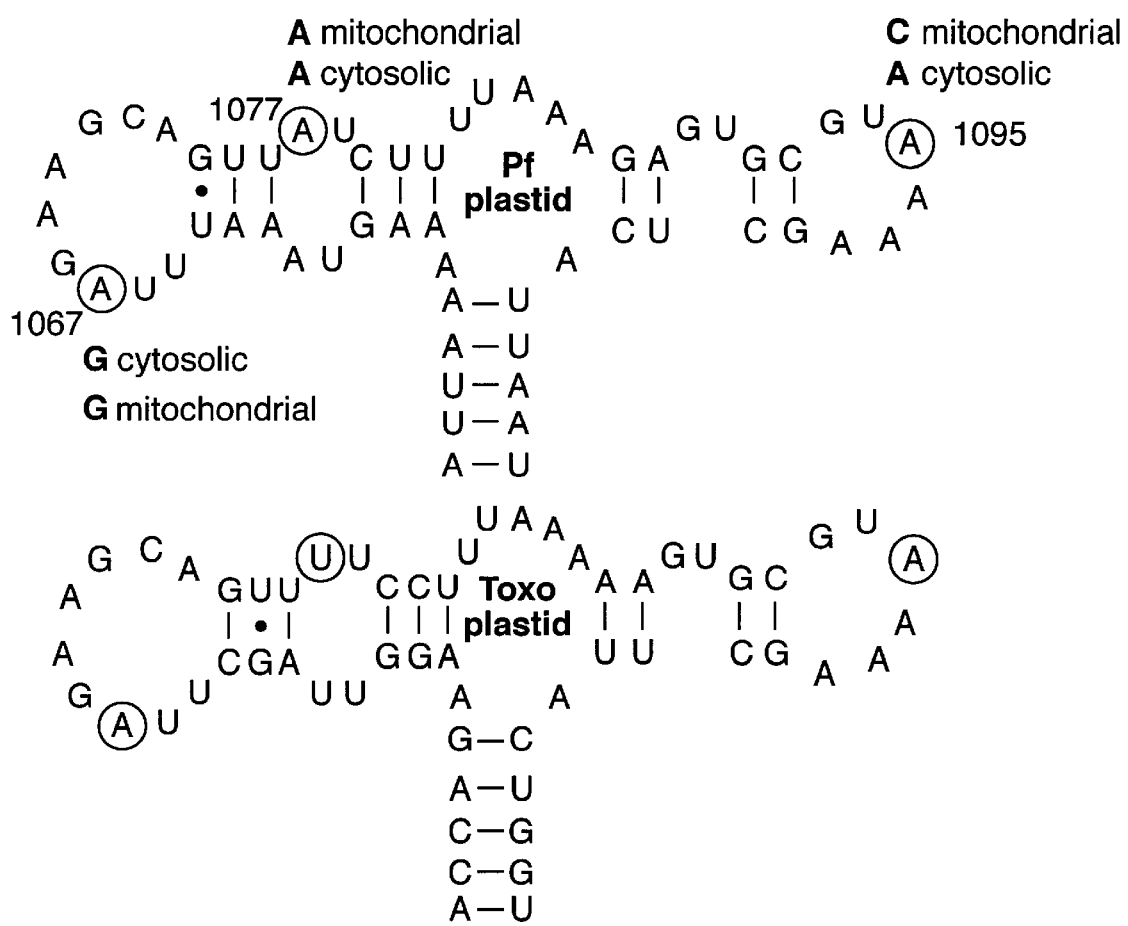
FIG. 7 shows the sequence of the GTPase region of the plastid 23S rRNAs of Plasmodium falciparum (Pf, SEQ ID NO:8) and Toxoplasma gondii (Toxo, SEQ ID NO:11) (numbers based on E. coli), showing substitution sites (circled) affecting the binding of thiostrepton. The alternative nucleotides in Pf cytosolic 28S rRNA (SEQ ID NO:9) and Pf mitochondrial 23S rRNA (SEQ ID NO:10) are indicated.

Thiostrepton: Nucleotide (nt) sequences are available for the GTPase domain of the 28S rRNA specified by the nucleus (Rogers et al. 1996), as well as the 23S rRNAs specified by the mt and pl large subunit rRNA genes of the human malaria pathogen $Plasmodium\ falciparum$ (Pf) (Feagin, 1992). These data indicate that the high affinity binding site for the thiazolyl peptide antibiotic thiostrepton, $A_{1067}$ in $E.coli$ (Thompson et al 1991, Ryan et al 1991 and Rosendahl et al 1994), is conserved in the GTPase domain encoded by the plastid DNA, but modified to a G in both nuclear and mitochondrial genomes (FIG. 7).

We have tested thiostrepton to ascertain whether it inhibits Pf and found reproducible inhibition of uptake of $^3$H-hypoxanthine and $^{14}$C-isoleucine in blood cultures (50% inhibition at 3–5µM thiostrepton). Onset of inhibition of protein synthesis by thiostrepton was more rapid (5 hrs) than by tetracycline (8 hrs). Specificity was demonstrated by the lack of effect of viomycin (data not shown), an unrelated antibiotic that also can inhibit translocation (Kutay et al 1990).

Figure 8A:
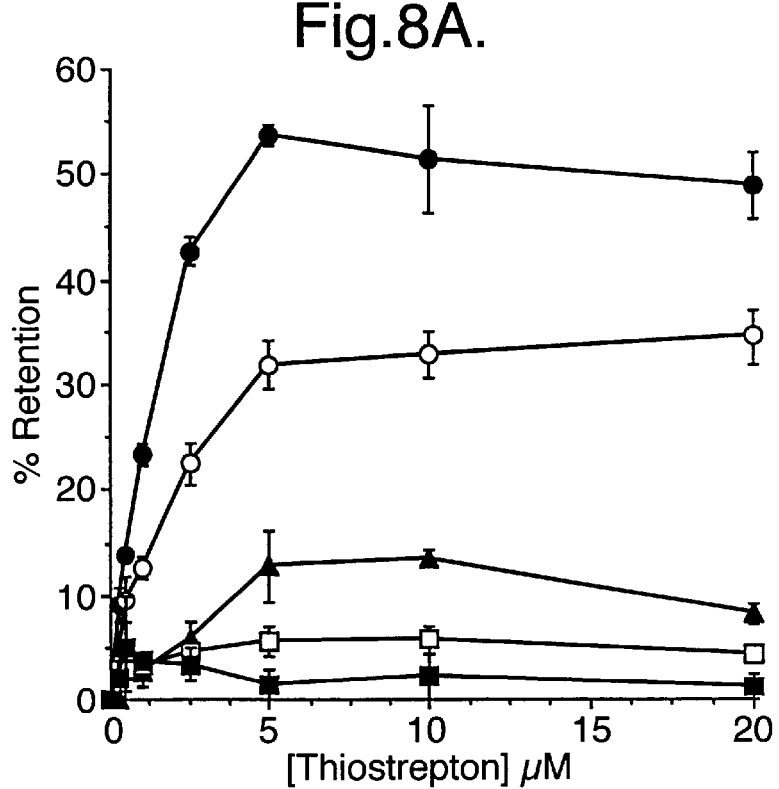
FIG. 8 shows thiostrepton titrations (means of duplicates, bar=range) in a filter binding assay with transcripts of the GTPase region of LSU rRNA. A) Short 23S transcripts of P.falciparum (Pf) wild type rRNA$_{pl}$ (open circle A1067) and mutated forms (open square A1067U and filled triangle A1067G), as well as Pf 28S rRNA transcripts (filled square), are compared with an optimized E.coli control transcript (filled circle). For convenience, nucleotide numbers correspond to E. coli. B) T. gondii wild type rRNA$_{pl}$ transcript (filled triangle) and mutated transcript (open triangle) compared with control transcripts from P.falciparum rRNA$_{pl}$ (open circle) and E.coli (filled circle).

Having established thiostrepton's activity, we asked "does the antibiotic bind preferentially to the nuclear, mitochondrial or plastid forms of Pf 28/23S rRNA?". Evidence that the highest affinity interaction of thiostrepton is with 23S rRNA$_{pl}$ was obtained from an in vitro binding assay (Ryan et al 1991). Short transcripts of wild type (wt) RNA corresponding to the GTPase domain of Pf 23S rRNA$_{pl}$ (nts 987–1078) were transcribed in vitro from a PCR product that included a T7 promoter sequence in one of the primers. Mutated malarial rRNA sequences ($E.coli$ numbers A1067U and A1067G) were obtained by PCR methodology and transcribed in the same way. Both wild type and modified transcript sequences were verified prior to thiostrepton binding assays. A positive control transcript was used based on the 23S rRNA sequence of $E.coli$ with a mutation (U1061A) that increases stability and binding. FIG. 8A shows that the mutation Pf$_{pl}$ ($E.coli$ number A1067U) markedly reduced thiostrepton binding (~14% of wt). An intermediate level of binding (~35% of wt) was obtained with the mutation Pf$_{pl}$ ($E.coli$ number A1067G). Thiostrepton binding to a transcript corresponding to the GTPase domain (nt 1334–1427) of the cytosolic Pf 28S rRNA was ~10% of that for Pf 23S rRNA$_{pl}$. These data show that the nts crucial for thiostrepton binding to Pf 23S rRNA are as in $E.coli$, and that the plastid form has the highest binding affinity.

Figure 8B:
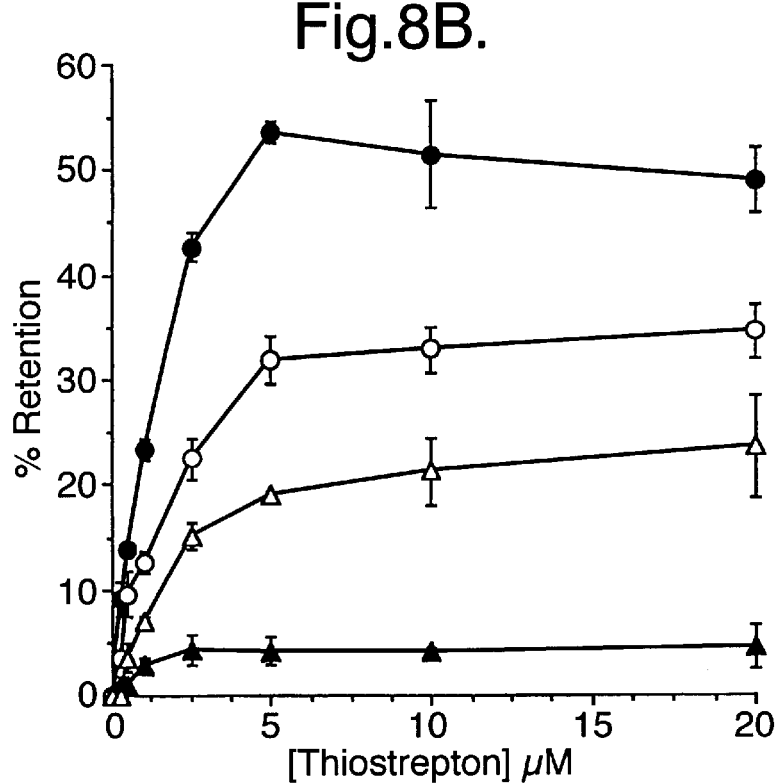
Figure 10:
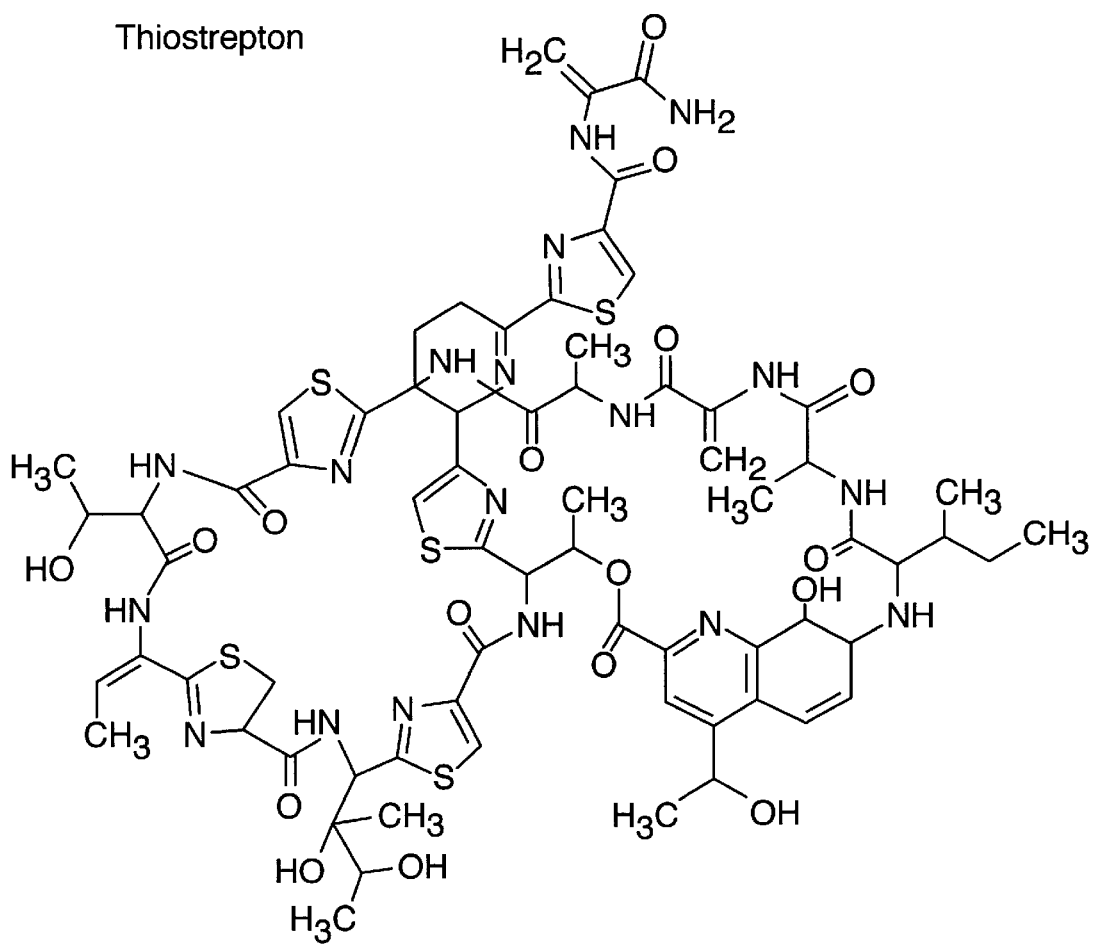

In the same way, we tested a transcript corresponding to the GTPase domain of the 23S rRNA$_{pl}$ of $Toxoplasma\ gondii$ (Tg), a related apicomplexan that is an important opportunistic pathogen in patients with AIDS. In this case, the wild type sequence has a substitution at a different site ($E.coli$ number A1077U)—see FIG. 7, that inhibits binding by thiostrepton in $E.\ coli$ (Ryan et al 1991). This was found also to be the case with a transcript derived from a PCR product covering the GTPase domain of Tg$_{pl}$ 23S rRNA (nt 926–1024) (FIG. 8B). Corrective mutation of the Tg$_{pl}$ transcript ($E.\ coli$ number U1077A) conferred a significant increase (×5) in thiostrepton binding (FIG. 8B).

These thiostrepton binding studies constitute the first direct evidence that components of the malarial plastid organelle could be preferentially targeted by drugs. The results complement earlier studies (Pfefferkon et al 1994 and Beckers et al 1995) which inferred that toxoplasma's 23S rRNA$_{pl}$ might be the target of the macrolide antiobiotic, clindamycin, acting at a different effector site.

Drugs Bind to Heterologously Expressed EF-TU

Figure 13A:
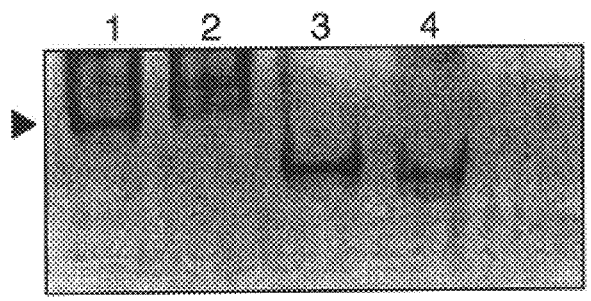
FIG. 13 contains immunoblots showing that binding of antibiotics modifies migration of EF-Tu.GDP in native polyacrylamide gels. Two segments of the same gel show A) heterologously expressed Pf EF-Tu$_{pl}$ protein detected with a malaria peptide-specific antibody and B) E.coli EF-Tu detected with a specific antibody (Breidenbach et al 1990). Lanes without antibiotics (1 and 5), lanes with 100 μM antibiotic: GE2270A (2 and 6), enacyloxin lla (3 and 7), kirromycin (4 and 8). Arrows indicate uncomplexed EF-Tu.
Figure 13B:
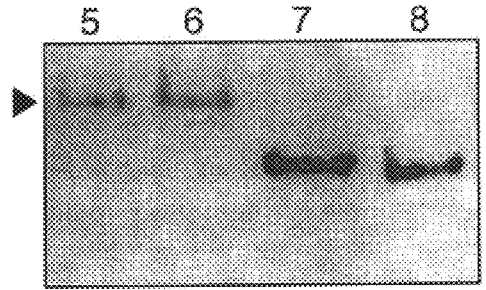

The material tufA gene in pGEX was expressed as an insoluble fusion protein in $E.coli$ JM 109. The protein was detected either with antibodies to the GST tag or with antibodies to a specific peptide sequence in domain I (IQKNKDYELIKSN SEQ ID NO:7) not found on *E.coli* EF-Tu. Washed inclusion bodies were dissolved and refolded by dilution (Lin et al 1991). This yielded a small amount of refolded protein that migrated in native acrylamide gels as a spontaneously cleaved product and we used this to show that the expressed protein forms complexes with kirromycin and other drugs that bind to different sites on EF-Tu. As shown in FIG. 13, the mobility ($M_r$) of the expressed malarial protein was advanced or retarded in these complexes in the same characteristic way described for *E.coli* EF-Tu (Cetin et al 1996): the $M_r$ of the GDP form of the complex decreased with GE2270A, but increased with enacyloxin IIa or kirromycin. These results show that the heterologously expressed Pf EF-Tu$_{pl}$ can adopt a native conformation and bind the classical antibiotic inhibitors.

References

Williamson et al., 1985. Mol. Biochem. Parasitol. 14, 199–209.
Williamson et al., 1994. Mol. Gen. Genet. 243, 249–252.
Gutteridge et al., 1971. Parasitology 62, 209–219.
Wilson et al., 1994. Infect. Agents Dis. 3, 29–37.
Wilson et al., 1991. Parasitol. Today 7, 134–136.
Wilson et al., 1992. Curr. Genet. 21, 405–408.
Vaidya et al., 1993. Mol. Cell. Biol. 13, 7349–7357.
Creasey et al., 1994. Mol. Biochem. Parasitol. 65, 95–98.
Kohler and Milstein, 1975. Nature 256, 495–497.
Kohler et al 1997 Science 275 1485–1489.
Montadon and Stutz, 1984 Nucl. Acids Res. 12, 2851–2859.
Hallick et al., 1993. Nucl. Acids Res. 21, 3537–3544.
Siemeister et al., 1990. Mol. Gen. Genet. 220, 425–432.
Douglas, 1991. Nature 350, 148–151.
Kraus et al., 1990. Plant Mol. Biol. 15, 561–573.
Zenge and Lindahl, 1990. Biochim.Biophys.Acta 1050, 317–322.
Nagata et al., 1983. Proc. Natl. Acad. Sci. USA 80, 6192–6196.
Piechulla and Kuntzel, 1983 Eur. J. Biochem. 132, 235–240.
Baldauf et al., 1990. Proc. Natl. Acad. Sci. USA 87, 5317–5321.
Wells et al., 1995. FEBS Letters 358, 119–125.
Mesters et al., 1994. EMBO J. 13, 4877–4885.
Schmid et al., 1978. FEBS Lett 96, 189–191.
Divo et al., 1985. Antimicrob. Agents Chemother. 27, 21–27.
Rogers et al., 1996. RNA 2, 134–145.
Feagin, 1992. Mol. Biochem. Parasitol. 52, 145–148.
Thompson et al., 1991. Biochimie 73, 1131–1135.
Ryan et al., 1991. J. Mol. Biol. 221, 1257–1268.
Rosendahl et al., 1994. Nucl. Acids Res. 22, 357–363.
Kutay et al., 1990. Biochim. Biophys. Acta 1050, 193–196.
Pfefferkorn et al., 1994. Antimicrob. Agents Chemother. 38, 31–37.
Beckers et al., 1995. J. Clin. Invest. 95, 367–376.
Wilson et al (1996) J. Mol. Biol. 261, 155–172.
Trager, et al (1976) Science 193, 673–675.
Sherman et al (1975) J. Protozool. 22, 568–572.
Cox, (1969) Biochem. J. 114, 753–767.
Cundliffe, et al (1974) Proc. Natl. Acad. Sci. USA 71, 30–34.
Chomczynski et al (1987) Anal. Biochem. 162, 156–159.
McCutchen, et al (1988) Mol. Biochem. Parasitol. 28, 63–68.
Grande et al (1977) Parasitology 115, 81–89.
Bodanszky et al (1965) in US Patent Office, U.S. Pat. No. 3,181,995.
Strath et al (1993) Trans. R. Soc. Trop. Med. Hyg. 87, 211–216.
Berchtold et al (1993) Nature 365, 126–132.
Polekhina et al (1996) Structure 4, 1141–1151.
Vriend (1990) J. Mol. Graph. 8, 52–56.
Tews et al (1 996) Nature Struct. Biol. 3, 638–648.
Lin et al (1991) Biotechniques 11, 748–752.
Ryan et al (1991) J. Mol. Biol. 221, 1257–1268.
Clough et al (1997) FEBS Letters 406, 123–125.
Cetin et al (1996) The EMBO J. 15, 2604–2611.
Gale et al (1981) The Molecular Basis of Antibiotic Action. John Wiley & Sons Ltd., London.
Abdulkarim et al (1994) FEBS Letters 352,118–122.
Watanabe et al (1992) J. Antibiot. 45, 470–475.
Landini et al (1996) Biochemistry 35, 15288–15294.
Breidenbach et al (1990) Biochim. Biophys Acta 1048, 209–216.

We claim:

1. A method for screening a compound for anti-malarial activity with malarial elongation factor-Tu(EF-Tu) protein, which method comprises (i) contacting the compound with the EF-Tu protein encoded on the 35 kb circular plastid DNA of *Plasmodium falciparum*; and (ii) determining whether the compound binds to and inhibits the protein, any such binding and inhibition suggesting that the compound may have anti-malarial activity.

2. The method of claim 1 wherein the EF-Tu protein has a sequence labelled "eftu-pf" in FIG. 2A (SEQ ID NO: 2).

* * * * *